United States Patent
Sims et al.

(10) Patent No.: US 9,346,870 B2
(45) Date of Patent: *May 24, 2016

(54) ANTIBODIES THAT INHIBIT TSLP ACTIVITY

(71) Applicant: IMMUNEX CORPORATION, Thousand Oaks, CA (US)

(72) Inventors: John E. Sims, Seattle, WA (US); Stewart D. Lyman, Seattle, WA (US); Hilary J. McKenna, Tauranga RD3 (NZ); Allison P. Jacob, Seattle, WA (US)

(73) Assignee: IMMUNEX CORPORATION, Thousand Oaks, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/487,564

(22) Filed: Sep. 16, 2014

(65) Prior Publication Data

US 2015/0005226 A1    Jan. 1, 2015

Related U.S. Application Data

(60) Continuation of application No. 13/887,893, filed on May 6, 2013, now abandoned, which is a continuation of application No. 13/243,837, filed on Sep. 23, 2011, now Pat. No. 8,444,979, which is a continuation of application No. 12/822,050, filed on Jun. 23, 2010, now abandoned, which is a continuation of application No. 12/220,879, filed on Jul. 28, 2008, now Pat. No. 7,786,271, which is a continuation of application No. 11/452,762, filed on Jun. 13, 2006, now Pat. No. 7,405,058, which is a division of application No. 10/376,406, filed on Feb. 27, 2003, now Pat. No. 7,304,144, which is a division of application No. 09/852,391, filed on May 9, 2001, now Pat. No. 6,555,520, which is a continuation of application No. PCT/US99/27069, filed on Nov. 12, 1999.

(60) Provisional application No. 60/108,452, filed on Nov. 13, 1998.

(51) Int. Cl.
| | |
|---|---|
| *A61K 38/40* | (2006.01) |
| *A61K 38/00* | (2006.01) |
| *C07K 14/52* | (2006.01) |
| *C07K 14/475* | (2006.01) |
| *C07K 14/54* | (2006.01) |
| *C07K 16/24* | (2006.01) |
| *C12N 5/0783* | (2010.01) |

(52) U.S. Cl.
CPC .............. *C07K 14/52* (2013.01); *C07K 14/475* (2013.01); *C07K 14/5418* (2013.01); *C07K 16/24* (2013.01); *C12N 5/0636* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,011,912 | A | 4/1991 | Hopp et al. |
| 6,555,520 | B2 | 4/2003 | Sims et al. |
| 6,844,170 | B1 | 1/2005 | Moore et al. |
| 7,304,144 | B2 | 12/2007 | Sims et al. |
| 7,405,058 | B2 | 7/2008 | Sims et al. |
| 7,786,271 | B2 | 8/2010 | Sims et al. |
| 8,444,979 | B2 | 5/2013 | Sims et al. |
| 2002/0146819 | A1 | 10/2002 | Sims et al. |
| 2003/0099947 | A1 | 5/2003 | Bazan et al. |
| 2003/0186875 | A1 | 10/2003 | De Waal Malefyt et al. |
| 2005/0249712 | A1 | 11/2005 | Leonard et al. |
| 2009/0186022 | A1 | 7/2009 | Bardroff et al. |
| 2010/0266601 | A1 | 10/2010 | Sims et al. |

FOREIGN PATENT DOCUMENTS

| | | |
|---|---|---|
| WO | WO-93/21946 A1 | 11/1993 |
| WO | WO-95/00103 A2 | 1/1995 |
| WO | WO-98/36061 A2 | 8/1998 |
| WO | WO-99/47538 A1 | 9/1999 |
| WO | WO-00/17362 A1 | 3/2000 |
| WO | WO-00/29581 A1 | 5/2000 |
| WO | WO-00/39149 A2 | 7/2000 |
| WO | WO-01/12672 A2 | 2/2001 |
| WO | WO-01/62272 A2 | 8/2001 |
| WO | WO-01/87328 A2 | 11/2001 |
| WO | WO-02/00723 | 1/2002 |
| WO | WO-02/00724 | 1/2002 |
| WO | WO-03/065985 A2 | 8/2003 |
| WO | WO-03/099823 A2 | 12/2003 |
| WO | WO-2004/022718 A2 | 3/2004 |
| WO | WO-2005/007186 A1 | 1/2005 |

(Continued)

OTHER PUBLICATIONS

Allakhverdi et al., Thymic stromal lymphopoietin is released by human epithelial cells in response to microbes, trauma, or inflammation and potently activates mast cells, *J. Exp. Med.*, 204(2):253-8 (2007).

Barnes et al., New therapeutic approaches, *Br. Med. Bull.*, 48(1):231-47 (1992).

Barnes, Corticosteroid effects on cell signaling, *Eur. Respir. J.*, 27(2):413-26 (2006).

Bazan, Haemopoietic receptors and helical cytokines, *Immunol. Today*, 11:350-4 (1990).

(Continued)

*Primary Examiner* — Olga N Chernyshev
(74) *Attorney, Agent, or Firm* — Marshall, Gerstein & Borun LLP

(57) ABSTRACT

The invention is directed to purified and isolated novel TSLP polypeptides, the nucleic acids encoding such polypeptides, processes for production of recombinant forms of such polypeptides, antibodies generated against these polypeptides, fragmented peptides derived from these polypeptides, and the uses of the above.

12 Claims, 2 Drawing Sheets

(56) References Cited

FOREIGN PATENT DOCUMENTS

| WO | WO-2006/023791 A2 | 3/2006 |
|----|-------------------|--------|
| WO | WO-2007/096149 A1 | 8/2007 |

OTHER PUBLICATIONS

Blyth et al., Airway subepithelial fibrosis in a murine model of atopic asthma: suppression by dexamethasone or antiinterleukin-5 antibody, *Am. J. Respir. Cell. Mol. Biol.*, 23(2):241-6 (2000).
Borish et al., Efficacy of soluble IL-4 receptor for the treatment of adults with asthma, *J. Allergy Clin. Immunol.*, 107 (6):963-70, 2001.
Bork et al., Go hunting in sequence databases but watch out for the traps, *Trends Genet.*, 12:425-7 (1996).
Bork, Powers and pitfalls in sequence analysis: the 70% hurdle, *Genome Res.*, 10:398-400 (2000).
Brenner, Errors in genome annotation, *Trends Genet.*,15:132-3 (1999).
Burdach et al., The physiologic role of interleukin-3, interleukin-5, granulocyte-macrophage colonystimulating factor, and the β c receptor system, *Curr. Opin. Hematol.*, 5:177-80 (1998).
Candeias et al., IL-7 receptor and VDJ recombination: trophic versus mechanistic actions, *Immunity*, 6:501-8 (1997).
Candeias, et al., Defective T-cell receptor γ gene rearrangement in interleukin-7 receptor knockout mice, *Immunol. Lett.*, 57:9-14 (1997).
Cao et al., Characterization of cDNAs encoding the murine interleukin 2 receptor (IL-2R) γchain: chromosomal mapping and tissue specificity of IL-2R γchain expression, *Proc. Natl. Acad. Sci. USA*, 90:8464-8 (1993).
Carpino, Absence of an essential role for thymic stromal lymphopoietin receptor in murine B cell development, *Mol. Cell Biol.*, 24(6):2584-92 (2004).
Cohn et al., T helper 1 cells and interferon gamma regulate allergic airway inflammation and mucus production, *J. Exp. Med.*, 190(9):1309-17 (1999).
Corrigan et al., Early production of thymic stromal lymphopoietin precedes infiltration of dendritic cells expressing its receptor in allergen-induced late phase cutaneous responses in atopic subjects, *Allergy*, 64:1014-22 (2009).
Cunningham and Wells, High-resolution epitope mapping of hGH-receptor interactions by alaninescanning mutagenesis, *Science*, 244:1081-5 (1989).
Database EMBL Online Accession No. AB031333, Kitamura and Fujio, Mus musculus mRNA for cytokine receptor deltal, complete cds, Feb. 24, 2000.
Database EMBL Online Accession No. AB039945, Hiroyama et al., Mus musculus CRLM2 mRNA for cytokine receptor like molecule 2, complete cds, Mar. 14, 2000.
Database EST, Accession No. AA021949, Marra et al., Marra M/Mouse EST Project, Jan. 21, 1997.
Database EST, Accession No. AA889581, EST; *H. sapiens* cDNA clone IMAGE: 1407260, Apr. 6, 1998.
Davies, The role of the epithelium in airway remodeling in asthma, *Proc. Am. Thorac. Soc.* 6:678-82 (2009).
Doerks et al., Protein annotation: detective work for function prediction, Trends Genet., 14:248-50 (1998).
DosReis et al., The central role of Fas-ligand cell signaling in inflammatory lung diseases, *J. Cell. Mol. Med.*, 8(3):285-93 (2004).
Edwards et al., Therapy directed against thymic stromal lymphopoietin, *Drug News Perspect*, 21(6):312-6 (2008).
Friend et al., Initial characterization of Thymic Stromal Derived Lymphopoietin (TSLP), *FASEB. J.*, 8:A506 (1994). (Abstract).
Friend et al., A thymic stromal cell line supports in vitro development of surface IgM+ B cells and produces a novel growth factor affecting B and T lineage cells, *Exp Hematol.*, 22(3):321-28 (1994).
Fujio et al., Molecular cloning of a novel type I cytokine receptor similar to the common gamma chain, *Blood*, 95(7):2204-11 (2000).
Gao et al., Establishment of allergic dermatitis in NC/Nga mice as a model for severe atopic dermatitis, *Biol. Pharm. Bull.*, 27(9):1376-81 (2004).
Garcia et al., Evaluation of inflammatory cytokine secretion by human alveolar macrophages, *Mediators Inflamm.*, 8(1):43-51 (1999).
Giri et al., Utilization of the β and γchains of the IL-2 receptor by the novel cytokine IL-15, *EMBO J.*, 13:2822-30 (1994).
Grunewald et al., An antagonistic IL-4 mutant prevents Type I allergy in the mouse: inhibition of the IL-4/IL-13 receptor system completely abrogates humoral immune response to allergen and development of allergic symptoms in vivo, *J. Immunol.*, 160(8):4004-9 (1998).
Guthridge et al., Mechanism of activation of the GM-CSF, IL-3, and IL-5 family of receptors, *Stem Cells* ,16:301-13 (1998).
He et al., A thymic stromal lymphopoietin gene variant is associated with asthma and airway hyperresponsiveness, *J. Allergy Clin. Immunol.*, 10.1016 (2009).
He et al., Small-molecule inhibition of TNF-α, *Science*, 310(5750):1022-5 (2005).
He et al., The common γ-chain of cytokine receptors regulates intrathymic T cell development at multiple states, *J. Immunol.*, 158:2592-9 (1997).
Hirano et al., Signaling mechanisms through gp130: a model of the cytokine system, *Cytokine Growth Factor Rev* ., 8:241-52 (1997).
Hiroyama et al., Molecular cloning and characterization of CRLM-2, a novel type I cytokine receptor preferentially expressed in hematopoietic cells, *Biochem. Biophys. Res. Commun.* 272(1):224-9 (2000).
Hosaka, et al., Arg-X-Lys/Arg-Arg Motif as a signal for precursor cleavage catalyzed by furin within the constitutive secretory pathway, *J. Biol. Chem.*, 266(19):12127-30 (1991).
Huang, Structural chemistry and therapeutic intervention of protein-protein interactions in immune response, human immunodeficiency virus entry, and apoptosis, *Pharmacol. Ther.*, 86(3):201-15 (2000).
Ichinose et al., Cytokine-directed therapy in asthma, *Curr. Drug Targets Inflamm. Allergy*, 3(3):263-9 (2004).
Isaksen et al., Requirement for stat5 in thymic stromal lymphopoietin-mediated signal transduction, *J. Immunol.*, 163(11):5971-7 (1999).
Jakubzick et al., Therapeutic targeting of IL-4- and IL-13-responsive cells in pulmonary fibrosis, *Immunol. Res.*, 30(3):339-49 (2004).
Jessup et al., Intradermal administration of thymic stromal lymphopoietin induces a T cell- and eosinophil-dependent systemic Th2 inflammatory response, *J. Immunol.*, 181:4311-9 (2008).
Kimura et al., Sharing of the IL-2 receptor y chain with the functional IL-9 receptor complex, *Int. Immunol.*, 7:115-20 (1995).
Kobayashi et al., Cloning and sequencing of the cDNA encoding a mouse IL-2 receptor γ, *Gene*, 130:303-4 (1993).
Kondo et al., Functional participation of the IL-2 receptor γ chain in IL-7 receptor complexes, *Science*, 263:1453-4 (1994).
Kondo et al., Sharing of the interleukin-2 (IL-2) receptor γ chain between receptors for IL-2 and IL4, *Science*, 262:1874-7 (1993).
Kowalewska et al., Thymic stromal lymphopoietin transgenic mice develop cryoglobulinemia and hepatitis with similarities to human hepatitis C liver disease, *Am. J. Pathol.*, 170:981-9 (2007).
Lai, L. et al., Identification of an IL-7 associated pre-pro-B cell growth-stimulating factor (PPBSF) II. PPBSF is a covalently linked heterodimer of IL-7 and a Mr 30,000 Co-factorl, *J. Immunol.*, 160:2280-6 (1998).
Lambrecht and Hammad, Taking our breath away: dendritic cells in the pathogenesis of asthma, *Nat. Rev. Immunol.*, 3:994-1003 (2003).
Leckie et al., Effects of an interleukin-5 blocking monoclonal antibody on eosinophils, airway hyperresponsiveness, and the late asthmatic response, *Lancet*, 356:2144-8 (2000).
Lee et al., Normal B cell precursors responsive to recombinant murine IL-7 and inhibition of IL-7 activity by transforming growth factor-β, *J Immunol* 142:3875-83 (1989).
Leonard et al., JAKS and STATS: Biological implications, *Annu. Rev. Immunol.*, 16:293-322 (1998).
Leonard et al., Role of the common cytokine receptor γ chain in cytokine signaling and lymphoid development, *Immunol Rev* 148:97-114, 1995.

(56) References Cited

OTHER PUBLICATIONS

Leonard, Chapter 21. Type I cytokines and interferons and their receptors, *Fundam Immunol* (Paul, ed., Lippincott Raven Publishers 4 Ed.), pp. 741-774 (1999).
Leonard, TSLP: finally in the limelight, *Nat. Immunol.*, 3(7):605-7 (2002).
Levin et al., Thymic Stromal Lymphopoietin: A cytokine that promotes the development of IgM+ B cells in vitro and signals via a novel mechanism, *J. Immunol.*, 162:677-83 (1999).
Li et al., Identification of the CD8 DE loop as a surface functional epitope, *J. Biol. Chem.* 273(26):16442-5 (1998).
Liu, Thymic stromal lymphopoietin: master switch for allergic inflammation, *J. Exp. Med.* 203(2):269-73 (2006).
Marchal-Somme et al., Dendritic cells accumulate in human fibrotic interstitial lung disease, *Am. J. Respir. Crit. Care Med.*, 176:1007-14 (2007).
Menneki, The role of TSLP for B cell lymphopoesis, *Immunol Frontier*, 10(2):40-3 (2000). (with partial English translation).
Mikayama et al., Molecular cloning and functional expression of a cDNA encoding glycosylationinhibiting factor, *Proc. Natl. Acad. Sci., USA* 90:10056-60 (1993).
Miyajima et al., Signal transduction by the GM-CSF, IL-3 and IL-5 receptors, *Leukemia*, 11(Supp13):418-22 (1997).
Nelson et al., Cytoplasmic domains of the interleukin-2 receptor β and γchains mediate the signal for T-cell proliferation, *Nature*, 369:333-6 (1994).
Noguchi et al., Interleukin-2 receptor γchain mutation results in X-linked severe combined immunodeficiency in humans, *Cell*, 73:147-57 (1993).
Noguchi et al., Interleukin-2 receptor γchain: a functional component of the interleukin-7 receptor, *Science*, 262:1877-80 (1993).
Ong et al., Anti-IL-4 treatment prevents dermal collagen deposition in the tight-skin mouse model of scleroderma, *Eur. J. Immunol.*, 28(9):2619-29 (1998).
Pandey et al., Cloning of a receptor subunit required for signaling by thymic stromal lymphopoietin, *Nat. Immunol.*, 1(1):59-64 (2000).
Pape et al., Inflammatory cytokines enhance the in vivo clonal expansion and differentiation of antigen-activated CD4+T cells, *J. Immunol* 159(2):591-8 (1997).
Pape et al., Use of adoptive transfer of T-cell-antigen-receptor-transgenic T cells for the study of Tcell activation in vivo, *Immunol. Rev.* 156:67-78 (1997).
Park et al., Cloning of the murine thymic stromal lymphopoietin (TSLP) receptor: formation of a functional heteromeric complex requires interleukin 7 receptor, *J. Exp. Med.*, 192 (5):659-69 (2000).
Peschon et al., Early lymphocyte expansion is severely impaired in interleukin 7 receptor-deficient mice, *J. Exp. Med.*, 180:1955-60 (1994).
Quentmeier et al., Cloning of human thymic stromal lymphopoietin (TSLP) and signaling mechanisms leading to proliferation, *Leukemia*, 15:1286-92 (2001).
Ramalingam et al., Regulation of helminth-induced Th2 responses by thymic stromal lymphopoietin, *J. Immunol.*, 182:6452-9 (2009).
Ray et al., Characterization of thymic stromal-derived lymphopoietin (TSLP) in murine B cell development in vitro, *Eur. J. Immunol.*, 26:10-6 (1996).
Reche et al., Human thymic stromal lymphopoietin preferentially stimulates myeloid cells, *J. Immunol.*, 167:336-43 (2001).
Russell et al., Interaction of IL-2Rβ and γc chains with JakI and Jak3: implications for XSCID and XCID, *Science*, 266:1042-5 (1994).
Russell et al., Interleukin-2 receptor γ chain: a functional component of the interleukin-4 receptor, *Science*, 262:1880-3 (1993).
Semlali et al., Thymic stromal lymphopoietin-induced human asthmatic airway epithelial cell proliferation through an IL-13-dependent pathway, *J. Allergy Clin. Immunol.*, 125:844-50 (2010).
Shimizu et al., the appearance of 5-100 protein-positive dendritic cells and the distribution of lymphocyte subsets in idiopathic non-specific interstitial pneumonia, *Respir. Med.* 96:770-6 (2002).
Sims et al., Molecular cloning and biological characterizations of a novel murine lymphoid growth factor, *J. Exp. Med.*, 192(5):671-80 (2000).
Sin et al., Pharmacological management to reduce exacerbations in adults with asthma: a systematic review and meta-analysis, *JAMA*, 292(3):367-76 (2004).
Singh et al., Anti-TNF-alpha strategy: present status of this therapeutic paradigm, *Indian J. Pharmacol.*, 36(1):10-4 (2004).
Soumelis et al., Human thymic stromal lymphopoietin: a novel epithelial cell-derived cytokine and a potential key player in the induction of allergic inflammation, *Springer Semin. Immunopathol.*, 25:325-33 (2004).
Soumelis et al., Human epithelial cells trigger dendritic cell mediated allergic inflammation by producing TSLP, *Nat. Immunol.*, 3(7):673-80 (2002).
Suda et al., A stimulatory effect of recombinant murine interleukin-7 (IL-7) on B-cell colony formation and an inhibitory effect of IL-Ia, *Blood*,74:1936-41, 1989.
Sudo et al., Interleukin 7 production and function in stromal cell-dependent B cell development, *J. Exp. Med.*, 170:333-8 (1989).
Taga and Kishimoto, GP130 and the interleukin-6 family of cytokines, *Annu. Rev. Immunol.* 15:797-819 (1997).
Takeshita et al., Cloning of they chain of the human IL-2 receptor, *Science* 257:379-82 (1992).
von Freeden-Jeffrey et al., Lymphopenia in interleukin (IL)-7 gene-deleted mice identifies IL-7 as a nonredundant cytokine, *J. Exp. Med.*, 181:1519-26 (1995).
Wells, Additivity of mutational effects in proteins, *Biochemistry*, 29(37):8509-17 (1990).
Williams et al., Identification of spontaneous feline idiopathic pulmonary fibrosis, *Chest*, 125:2278-88 (2004).
Wilson et al., Pulmonary fibrosis: pathogenesis, etiology and regulation, *Mucosal Immunol.*, 2(2):103-21 (2009).
Wynn, Fibrotic disease and the TH1/TH2 paradigm, *Nat Rev Immunol* 4(8):583-94 (2004).
Zhou et al., Thymic stromal lymphopoietin as a key initiator of allergic airway inflammation in mice, *Nat. Immunol.*, 6:1047-53 (2005).
Ziegler et al., Thymic stromal lymphopoietin in normal and pathogenic T cell development and function, *Nat. Immunol.*, 7(7):709-14 (2006).
Ziegler et al., Reconstitution of a functional interleukin (IL)-7 receptor demonstrates that the IL-2 receptor y chain is required for IL-7 signal transduction, *Eur. J. Immunol.*, 25:399-404 (1995).

Name: TSLP

```
  1  GCAGCCAGAA AGCTCTGGAG CATCAGGGAG ACTCCAACTT AAGGCAACAG
 51  CATGGGTGAA TAAGGGCTTC CTGTGGACTG GCAATGAGAG GCAAAACCTG
101  GTGCTTGAGC ACTGGCCCCT AAGGCAGGCC TTACAGATCT CTTACACTCG
151  TGGTGGGAAG AGTTTAGTGT GAAACTGGGG TGGAATTGGG TGTCCACGTA
201  TGTTCCCTTT TGCCTTACTA TATGTTCTGT CAGTTTCTTT CAGGAAAATC
251  TTCATCTTAC AACTTGTAGG GCTGGTGTTA ACTTACGACT TCACTAACTG
301  TGACTTTGAG AAGATTAAAG CAGCCTATCT CAGTACTATT TCTAAAGACC
351  TGATTACATA TATGAGTGGG ACCAAAAGTA CCGAGTTCAA CAACACCGTC
401  TCTTGTAGCA ATCGGCCACA TTGCCTTACT GAAATCCAGA GCCTAACCTT
451  CAATCCCACC GCCGGCTGCG CGTCGCTCGC CAAAGAAATG TTCGCCATGA
501  AAACTAAGGC TGCCTTAGCT ATCTGGTGCC CAGGCTATTC GGAAACTCAG
551  ATAAATGCTA CTCAGGCAAT GAAGAAGAGG AGAAAAAGGA AAGTCACAAC
601  CAATAAATGT CTGGAACAAG TGTCACAATT ACAAGGATTG TGGCGTCGCT
651  TCAATCGACC TTTACTGAAA CAACAGTAAA CCATCTTTAT TATGGTCATA
701  TTTCACAGCC CAAAATAAAT CATCTTTATT AAGTAAAAAA AAA
(SEQ ID NO:1)
```

Figure 1

Name: TSLP (polypeptide)

```
  1 MFPFALLYVL SVSFRKIFIL QLVGLVLTYD FTNCDFEKIK AAYLSTISKD
 51 LITYMSGTKS TEFNNTVSCS NRPHCLTEIQ SLTFNPTAGC ASLAKEMFAM
101 KTKAALAIWC PGYSETQINA TQAMKKRRKR KVTTNKCLEQ VSQLQGLWRR
151 FNRPLLKQQ (SEQ ID NO:2)
```

Figure 2

ANTIBODIES THAT INHIBIT TSLP ACTIVITY

CROSS REFERENCE TO RELATED APPLICATIONS

This application is a continuation of U.S. Ser. No. 13/887,893, filed May 6, 2013, which is a continuation of U.S. Ser. No. 13/243,837, filed Sep. 23, 2011, now issued U.S. Pat. No. 8,444,979, which is a continuation of U.S. Ser. No. 12/822,050, filed Jun. 23, 2010, pending, which is a continuation of U.S. Ser. No. 12/220,879, filed Jul. 28, 2008, now issued U.S. Pat. No. 7,786,271, which is a continuation of U.S. Ser. No. 11/452,762, filed Jun. 13, 2006, now issued U.S. Pat. No. 7,405,058, which is a divisional of U.S. Ser. No. 10/376,406, filed Feb. 27, 2003, now issued U.S. Pat. No. 7,304,144, which is a divisional of U.S. Ser. No. 09/852,391, filed May 9, 2001, now issued U.S. Pat. No. 6,555,520, which is a continuation of PCT/US99/27069 filed Nov. 12, 1999, which claims the benefit of U.S. provisional application Ser. No. 60/108,452, filed Nov. 13, 1998, the entire disclosure of which is relied upon and incorporated by reference herein.

REFERENCE TO THE SEQUENCE LISTING

The present application is being filed along with a Sequence Listing in electronic format. The Sequence Listing is provided as a file entitled 2881-US-CNT4_ST25.txt, created Sep. 23, 2011 which is 4 KB in size. The information in the electronic format of the Sequence Listing is incorporated herein by reference in its entirety.

BACKGROUND OF THE INVENTION

1. Field of the Invention

The invention is directed to purified and isolated novel human thymic stromal lymphopoietin (TSLP) polypeptides and fragments thereof, the nucleic acids encoding such polypeptides, processes for production of recombinant forms of such polypeptides, antibodies generated against these polypeptides, fragmented peptides derived from these polypeptides, and uses thereof.

2. Description of Related Art

Although B cell development has been extensively studied, there still remain gaps in the pathway leading from hematopoietic stem cells to mature B cells. It is recognized that cytokines influence and play a critical role in B cell development and growth. Known cytokines that influence B cell development include IL-2, IL-4, IL-5, IL-6, IL-7, IFN-gamma, and granulocyte-macrophage colony-stimulating factor (GM-CSF).

In recent years, a novel murine growth factor, designated thymic stromal lymphopoietin (TSLP), has been shown to play a role in B cell development and maturation. The cytokine activity of murine TSLP is very similar to that of IL-7, which is required during proliferation and survival of pre-B cells (Janeway et al., *Immuno Biology*, 2$^{nd}$ Ed. (1996)). Both of these cytokines have been shown to sustain NAGS/7 cells (Friend et al., *Exp. Hematol.*, 22:321-328 (1994)) and support B lymphopoiesis. In addition, mature B lymphocytes fail to develop in the absence of either IL-7 or murine TSLP. Moreover, it has been shown that murine TSLP can replace IL-7 in sustaining B cell proliferative responses (Ray et al., *Eur. J. Immunol.*, 26:10-16 (1996)). Thus, in the mouse system, TSLP has a significant function in B cell development.

Like IL-7, murine TSLP can also costimulate thymocytes and mature T cells (Friend et al., *Exp. Hematol.*, 22:321-328 (1994)). Studies with IL-7 receptor (IL-7R) knockout mice indicate that IL-7, TSLP, or both play a crucial role in controlling the rearrangement of the T cell receptor-gamma (TCRγ) locus, presumably by mediating accessibility of the TCRγ genes to the VDJ recombinase (Candeias et al., *Immunology Letters*, 57:9-14 (1997)). Thus, murine TSLP also plays a significant role in T cell development.

Murine TSLP receptors and IL-7 receptors both use the IL-7R α-chain as part of their signaling complexes (Levin et al., *J. Immunol.*, 162:677-683 (1999)). Despite the common IL-7R α-chain, however, IL-7 and TSLP appear to mediate their lymphopoietic effects through distinct mechanisms IL-7 induces activation of Stat5 and the Janus family kinases Jak1 and Jak3, whereas murine TSLP induces activation of Stat5, but not any of the known Janus family kinases (Levin et al., *J. Immunol.*, 162:677-683 (1999)).

Given the important function of murine TSLP and the significance of its role in B cell and T cell development and maturation in the mouse system, there is a need in the art to identify and isolate human TSLP and to study its role in human B cell and T cell development and maturation. In addition, in view of the continuing interest in lymphocyte development and the immune system, the discovery, identification, and roles of new proteins, such as human TSLP and its receptors, are at the forefront of modern molecular biology, biochemistry, and immunology. Despite the growing body of knowledge, there is still a need in the art for the identity and function of proteins involved in cellular and immune responses.

In another aspect, the identification of the primary structure, or sequence, of an unknown protein is the culmination of an arduous process of experimentation. In order to identify an unknown protein, the investigator can rely upon a comparison of the unknown protein to known peptides using a variety of techniques known to those skilled in the art. For instance, proteins are routinely analyzed using techniques such as electrophoresis, sedimentation, chromatography, sequencing and mass spectrometry.

In particular, comparison of an unknown protein to polypeptides of known molecular weight allows a determination of the apparent molecular weight of the unknown protein (T. D. Brock and M. T. Madigan, *Biology of Microorganisms*, pp. 76-77, Prentice Hall, 6th ed., (1991)). Protein molecular weight standards are commercially available to assist in the estimation of molecular weights of unknown protein (New England Biolabs Inc. Catalog:130-131 (1995)); (J. L. Hartley, U.S. Pat. No. 5,449,758). However, the molecular weight standards may not correspond closely enough in size to the unknown protein to allow an accurate estimation of apparent molecular weight. The difficulty in estimation of molecular weight is compounded in the case of proteins that are subjected to fragmentation by chemical or enzymatic means, modified by post-translational modification or processing, and/or associated with other proteins in non-covalent complexes.

In addition, the unique nature of the composition of a protein with regard to its specific amino acid constituents results in unique positioning of cleavage sites within the protein. Specific fragmentation of a protein by chemical or enzymatic cleavage results in a unique "peptide fingerprint" (D. W. Cleveland et al., *J. Biol. Chem.* 252:1102-1106 (1977); M. Brown et al., *J. Gen. Virol.* 50:309-316 (1980)). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, *Biology of Microorganisms*, pp. 76-77, Prentice Hall, 6d ed. (1991)).

Fragmentation of proteins is further employed for amino acid composition analysis and protein sequencing (P. Matsudiara, *J. Biol. Chem.*, 262:10035-10038 (1987); C. Eckerskorn et al., *Electrophoresis*, 9:830-838 (1988)), particularly the production of fragments from proteins with a "blocked" N-terminus. In addition, fragmented proteins can be used for immunization, for affinity selection (R. A. Brown, U.S. Pat. No. 5,151,412), for determination of modification sites (e.g. phosphorylation), for generation of active biological compounds (T. D. Brock and M. T. Madigan, *Biology of Microorganisms*, 300-301 (Prentice Hall, 6d ed., (1991)), and for differentiation of homologous proteins (M. Brown et al., *J. Gen. Virol.*, 50:309-316 (1980)).

In addition, when a peptide fingerprint of an unknown protein is obtained, it can be compared to a database of known proteins to assist in the identification of the unknown protein using mass spectrometry (W. J. Hemel et al., *Proc. Natl. Acad. Sci. USA* 90:5011-5015 (1993); D. Fenyo et al., *Electrophoresis*, 19:998-1005 (1998)). A variety of computer software programs to facilitate these comparisons are accessible via the Internet, such as Protein Prospector, MultiIdent, PeptideSearch, and ProFound. These programs allow the user to specify the cleavage agent and the molecular weights of the fragmented peptides within a designated tolerance. The programs compare these molecular weights to protein molecular weight information stored in databases to assist in determining the identity of the unknown protein. Accurate information concerning the number of fragmented peptides and the precise molecular weight of those peptides is required for accurate identification. Therefore, increasing the accuracy in determining of the number of fragmented peptides and the precise molecular weight should result in enhanced likelihood of success in the identification of unknown proteins.

In addition, peptide digests of unknown proteins can be sequenced using tandem mass spectrometry (MS/MS) and the resulting sequence searched against databases (J. K. Eng, et al., *J. Am. Soc. Mass Spec.* 5:976-989 (1994); M. Mann and M. Wilm, *Anal. Chem.*, 66:4390-4399 (1994); J. A. Taylor and R. S. Johnson, *Rapid Comm. Mass Spec.*, 11:1067-1075 (1997)). Searching programs that can be used in this process exist on the Internet, such as Lutefisk 97, and the Protein Prospector, Peptide Search and ProFound programs described above. Therefore, adding the sequence of a gene and its predicted protein sequence and peptide fragments to a sequence database can aid in the identification of unknown proteins using tandem mass spectrometry.

Thus, there also exists a need in the art for polypeptides suitable for use in peptide fragmentation studies, for use in molecular weight measurements, and for use in protein sequencing using tandem mass spectrometry.

SUMMARY OF THE INVENTION

The invention aids in fulfilling these various needs in the art by providing isolated human TSLP nucleic acids and polypeptides encoded by these nucleic acids. Particular embodiments of the invention are directed to an isolated TSLP nucleic acid molecule comprising the DNA sequence of SEQ ID NO:1 and an isolated TSLP nucleic acid molecule encoding the amino acid sequence of SEQ ID NO:2, as well as nucleic acid molecules complementary to these sequences. Both single-stranded and double-stranded RNA and DNA nucleic acid molecules are encompassed by the invention, as well as nucleic acid molecules that hybridize to a denatured, double-stranded DNA comprising all or a portion of SEQ ID NO:1. Also encompassed are isolated nucleic acid molecules that are derived by in vitro mutagenesis of the nucleic acid molecule comprising the sequence of SEQ ID NO:1, that are degenerate from the nucleic acid molecule comprising the sequence of SEQ ID NO:1, and that are allelic variants of DNA of the invention. The invention also encompasses recombinant vectors that direct the expression of these nucleic acid molecules and host cells transformed or transfected with these vectors.

In addition, the invention encompasses methods of using the nucleic acid noted above to identify nucleic acids encoding proteins having the ability to induce B lineage or T lineage cell proliferation; to identify human chromosome number 5; to map genes on human chromosome number 5; to identify genes associated with certain diseases, syndromes, or other human conditions associated with human chromosome number 5; and to study cell signaling and the immune system.

The invention also encompasses the use of sense or antisense oligonucleotides from the nucleic acid of SEQ ID NO:1 to inhibit the expression of the polynucleotide encoded by the TSLP gene.

The invention also encompasses isolated polypeptides and fragments thereof encoded by these nucleic acid molecules including soluble polypeptide portions of SEQ ID NO:2. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to study cellular processes such as immune regulation, cell proliferation, cell differentiation, cell death, cell migration, cell-to-cell interaction, and inflammatory responses. In addition, these polypeptides can be used to identify proteins associated with TSLP ligands and TSLP receptors.

In addition, the invention includes assays utilizing these polypeptides to screen for potential inhibitors of activity associated with polypeptide counter-structure molecules, and methods of using these polypeptides as therapeutic agents for the treatment of diseases mediated by TSLP polypeptide counter-structure molecules. Further, methods of using these polypeptides in the design of inhibitors thereof are also an aspect of the invention.

The invention further includes a method for using these polypeptides as molecular weight markers that allow the estimation of the molecular weight of a protein or a fragmented protein, as well as a method for the visualization of the molecular weight markers of the invention thereof using electrophoresis. The invention further encompasses methods for using the polypeptides of the invention as markers for determining the isoelectric point of an unknown protein, as well as controls for establishing the extent of fragmentation of a protein.

Further encompassed by this invention are kits to aid in these determinations.

Further encompassed by this invention is the use of the human TSLP nucleic acid sequences, predicted amino acid sequences of the polypeptide or fragments thereof, or a combination of the predicted amino acid sequences of the polypeptide and fragments thereof for use in searching an electronic database to aid in the identification of sample nucleic acids and/or proteins.

Isolated polyclonal or monoclonal antibodies that bind to these polypeptides are also encompassed by the invention, as well as the use of these antibodies to aid in purifying the TSLP polypeptide. In addition, the isolated antibodies can be used to establish an Enzyme-Linked Immunosorbent Assay (ELISA) to measure TSLP in samples such as serum.

BRIEF DESCRIPTION OF THE FIGURES

FIG. 1 presents the nucleotide sequence of human TSLP DNA (SEQ ID NO:1), and

FIG. 2 presents the amino acid sequence of human TSLP (SEQ ID NO:2).

DETAILED DESCRIPTION OF THE INVENTION

The nucleic acid molecules encompassed in the invention include the following nucleotide sequence:

```
Name: TSLP
                                              (SEQ ID NO: 1)
   1   GCAGCCAGAA AGCTCTGGAG CATCAGGGAG ACTCCAACTT
       AAGGCAACAG

51   CATGGGTGAA TAAGGGCTTC CTGTGGACTG GCAATGAGAG
       GCAAAACCTG

101   GTGCTTGAGC ACTGGCCCCT AAGGCAGGCC TTACAGATCT
       CTTACACTCG

151   TGGTGGGAAG AGTTTAGTGT GAAACTGGGG TGGAATTGGG
       TGTCCACGTA

201   TGTTCCCTTT TGCCTTACTA TATGTTCTGT CAGTTTCTTT
       CAGGAAAATC

251   TTCATCTTAC AACTTGTAGG GCTGGTGTTA ACTTACGACT
       TCACTAACTG

301   TGACTTTGAG AAGATTAAAG CAGCCTATCT CAGTACTATT
       TCTAAAGACC

351   TGATTACATA TATGAGTGGG ACCAAAAGTA CCGAGTTCAA
       CAACACCGTC

401   TCTTGTAGCA ATCGGCCACA TTGCCTTACT GAAATCCAGA
       GCCTAACCTT

451   CAATCCCACC GCCGGCTGCG CGTCGCTCGC CAAAGAAATG
       TTCGCCATGA

501   AAACTAAGGC TGCCTTAGCT ATCTGGTGCC CAGGCTATTC
       GGAAACTCAG

551   ATAAATGCTA CTCAGGCAAT GAAGAAGAGG AGAAAAAGGA
       AAGTCACAAC

601   CAATAAATGT CTGGAACAAG TGTCACAATT ACAAGGATTG
       TGGCGTCGCT

651   TCAATCGACC TTTACTGAAA CAACAGTAAA CCATCTTTAT
       TATGGTCATA

701   TTTCACAGCC CAAAATAAAT CATCTTTATT AAGTAAAAAA
       AAA
```

The amino acid sequence of the polypeptide encoded by the nucleotide sequence of the invention includes:

```
Name: TSLP (polypeptide)
                                              (SEQ ID NO: 2)
   1   MFPFALLYVL SVSFRKIFIL QLVGLVLTYD FTNCDFEKIK
       AAYLSTISKD

51   LITYMSGTKS TEFNNTVSCS NRPHCLTEIQ SLTFNPTAGC
       ASLAKEMFAM

101   KTKAALAIWC PGYSETQINA TQAMKKRRKR KVTTNKCLEQ
       VSQLQGLWRR

151   FNRPLLKQQ
```

The discovery of the nucleic acids of the invention enables the construction of expression vectors comprising nucleic acid sequences encoding polypeptides; host cells transfected or transformed with the expression vectors; isolated and purified biologically active polypeptides and fragments thereof; the use of the nucleic acids or oligonucleotides thereof as probes to identify nucleic acid encoding proteins having TSLP-like activity (e.g., inducing B lineage or T lineage cell proliferation), the use of the nucleic acids or oligonucleotides thereof to identify human chromosome number 5; the use of the nucleic acids or oligonucleotides thereof to map genes on human chromosome number 5; the use of the nucleic acid or oligonucleotides thereof to identify genes associated with certain diseases, syndromes or other human conditions associated with human chromosome number 5 and, in particular, with the q21-q22 region of chromosome number 5, including Gardner syndrome, adenomatous polyposis coli, hereditary desmoid disease, Turcot syndrome, and colorectal cancer; the use of single-stranded sense or antisense oligonucleotides from the nucleic acids to inhibit expression of polynucleotides encoded by the TSLP gene; the use of such polypeptides and soluble fragments to induce B lineage or T lineage cell proliferation; the use of such polypeptides and fragmented peptides as molecular weight markers; the use of such polypeptides and fragmented peptides as controls for peptide fragmentation, and kits comprising these reagents; the use of such polypeptides and fragments thereof to generate antibodies; and the use of the antibodies to purify TSLP polypeptides.

Nucleic Acid Molecules

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in (Sambrook et al., *Molecular Cloning: A Laboratory Manual*, 2nd sed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO:1, or a suitable fragment thereof, as a probe.

The DNA molecules of the invention include full length genes as well as polynucleotides and fragments thereof. The full length gene may also include the N-terminal signal peptide. Other embodiments include DNA encoding a soluble form, e.g., encoding the extracellular domain of the protein, either with or without the signal peptide.

The nucleic acids of the invention are preferentially derived from human sources, but the invention includes those derived from non-human species, as well.

Preferred Sequences

The particularly preferred nucleotide sequence of the invention is SEQ ID NO:1, as set forth above. A cDNA clone having the nucleotide sequence of SEQ ID NO:1 was isolated as described in Example 1. The sequence of amino acids encoded by the DNA of SEQ ID NO:1 is shown in SEQ ID NO:2. This sequence identifies the TSLP polynucleotide as a member of a group of factors that influence the growth of B lineage and T lineage cells (Ray et al., *Eur. J. Immunol*, 26:10-16 (1996)); (Friend et al., *Exp. Hematol.*, 22:321-328 (1994)).

Additional Sequences

Due to the known degeneracy of the genetic code, wherein more than one codon can encode the same amino acid, a DNA sequence can vary from that shown in SEQ ID NO:1, and still encode a polypeptide having the amino acid sequence of SEQ ID NO:2. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNA comprising the nucleotide sequence of SEQ ID NO:1; (b) DNA encoding the polypeptide of SEQ ID NO:2; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by (Sambrook et al. *Molecular Cloning: A Laboratory Manual*, 2ed. Vol. 1, pp. 1.101-104, Cold Spring Harbor Laboratory Press, (1989)), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42'C), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

Also included as an embodiment of the invention is DNA encoding polypeptide fragments and polypeptides comprising inactivated N-glycosylation site(s), inactivated protease processing site(s), or conservative amino acid substitution(s), as described below.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by (Devereux et al., *Nucl. Acids Res.*, 12:387 (1984)) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of (Gribskov and Burgess, *Nucl. Acids Res.*, 14:6745 (1986)), as described by (Schwartz and Dayhoff, eds., *Atlas of Protein Sequence and Structure*, National Biomedical Research Foundation, pp. 353-358 (1979)); (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding a human TSLP polypeptide, or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in (Saiki et al., *Science*, 239:487 (1988)); (Wu et al., *Recombinant DNA Methodology*, eds., Academic Press, Inc., San Diego, pp. 189-196 (1989)); and (Innis et al., *PCR Protocols: A Guide to Methods and Applications*, eds., Academic Press, Inc. (1990)).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

Polypeptides and Fragments Thereof

The polypeptides of the invention include full length proteins encoded by the nucleic acid sequences set forth above. Particularly preferred polypeptides comprise the amino acid sequence of SEQ ID NO:2 with particularly preferred fragments comprising amino acids 29 to 159 (the mature polypeptide sequence) of SEQ ID NO:2.

The polypeptide of SEQ ID NO:2 includes an N-terminal hydrophobic region that functions as a signal peptide. Computer analysis predicts that the signal peptide corresponds to residues 1 to 28 of SEQ ID NO:2 (although the next most likely computer-predicted signal peptide cleavage sites (in descending order) occur after amino acids 34 and 116 of SEQ ID NO:2). Cleavage of the signal peptide thus would yield a mature protein comprising amino acids 29 through 159 of SEQ ID NO:2.

The skilled artisan will recognize that the above-described boundaries of such regions of the polypeptide are approximate. To illustrate, the boundaries of the signal peptide (which may be predicted by using computer programs available for that purpose) may differ from those described above.

The polypeptides of the invention may be membrane bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In one embodiment, the soluble polypeptides and fragments thereof comprise all or part of the extracellular domain, but lack the transmembrane region that would cause retention of the polypeptide on a cell membrane. A soluble polypeptide may include the cytoplasmic domain, or a portion thereof, as long as the polypeptide is secreted from the cell in which it is produced.

Other embodiments include soluble fragments having an N-terminus at amino acids 29 or 35 and a C-terminus at amino acid 159.

In general, the use of soluble forms is advantageous for certain applications. Purification of the polypeptides from recombinant host cells is facilitated, since the soluble polypeptides are secreted from the cells. Further, soluble polypeptides are generally more suitable for intravenous administration.

The invention also provides polypeptides and fragments of the extracellular domain that retain a desired biological activity. Particular embodiments are directed to polypeptide fragments that retain the ability to bind TSLP receptors. Such a fragment may be a soluble polypeptide, as described above. In another embodiment, the polypeptides and fragments advantageously include regions that are conserved among the family of proteins that influence the growth of B lineage or T lineage cells described above.

Also provided herein are polypeptide fragments comprising at least 20, or at least 30, contiguous amino acids of the sequence of SEQ ID NO:2. Fragments derived from the cytoplasmic domain find use in studies of signal transduction, and in regulating cellular processes associated with transduction of biological signals. Polypeptide fragments also may be employed as immunogens, in generating antibodies.

Variants

Naturally occurring variants as well as derived variants of the polypeptides and fragments are provided herein.

Variants may exhibit amino acid sequences that are at least 80% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined by visual inspection and mathematical calculation. Alternatively, the percent identity of two protein sequences can be determined by comparing sequence information using the GAP computer program, based on the algorithm of (Needleman and Wunsch, *J. Mol. Bio.*, 48:443 (1970)) and available from the University of Wisconsin Genetics Computer Group (UWGCG). The preferred default parameters for the GAP program include: (1) a scoring matrix, blosum62, as described by (Henikoff and Henikoff *Proc. Natl. Acad. Sci. USA,* 89:10915 (1992)); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in (Hopp et al., *Bio/Technology,* 6:1204 (1988)). One such peptide is the FLAG[7] peptide, Asp-Tyr-Lys-Asp-Asp-Asp-Asp-Lys, (SEQ ID NO:3) which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG[7] peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG[7] peptide are available from Eastman Kodak Co., Scientific Imaging Systems Division, New Haven, Conn.

Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. No. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Oligomers

Encompassed by the invention are oligomers or fusion proteins that contain human TSLP polypeptides. Such oligomers may be in the form of covalently-linked or non-covalently-linked multimers, including dimers, trimers, or higher oligomers. As noted above, preferred polypeptides are soluble and thus these oligomers may comprise soluble polypeptides. In one aspect of the invention, the oligomers maintain the binding ability of the polypeptide components and provide therefor, bivalent, trivalent, etc., binding sites.

One embodiment of the invention is directed to oligomers comprising multiple polypeptides joined via covalent or non-covalent interactions between peptide moieties fused to the polypeptides. Such peptides may be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Immunoglobulin-Based Oligomers

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by (Ashkenazi et al., *PNAS USA*, 88:10535 (1991)); (Byrn et al., *Nature,* 344: 677 (1990)); and (Hollenbaugh and Aruffo "Construction of Immunoglobulin Fusion Proteins", in *Current Protocols in Immunology*, Suppl. 4, pp. 10.19.1-10.19.11 (1992)).

One embodiment of the present invention is directed to a dimer comprising two fusion proteins created by fusing a polypeptide of the invention to an Fc polypeptide derived from an antibody. A gene fusion encoding the polypeptide/Fc fusion protein is inserted into an appropriate expression vector. Polypeptide/Fc fusion proteins are expressed in host cells transformed with the recombinant expression vector, and allowed to assemble much like antibody molecules, whereupon interchain disulfide bonds form between the Fc moieties to yield divalent molecules.

The term "Fc polypeptide" as used herein includes native and mutein forms of polypeptides made up of the Fc region of an antibody comprising all of the CH domains of the Fc region. Truncated forms of such polypeptides containing the hinge region that promotes dimerization are also included. Preferred polypeptides comprise an Fc polypeptide derived from a human IgG1 antibody.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in (Baum et al., *EMBO J.,* 13:3992-4001 (1994)) incorporated herein by reference. The amino acid sequence of this mutein is identical to that of the native Fe sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns In other embodiments, the polypeptides of the invention may be substituted for the variable portion of an antibody heavy or light chain. If fusion proteins are made with both heavy and light chains of an antibody, it is possible to form an oligomer with as many as four TSLP extracellular regions.

Peptide-linker Based Oligomers

Alternatively, the oligomer is a fusion protein comprising multiple polypeptides, with or without peptide linkers (spacer peptides). Among the suitable peptide linkers are those described in U.S. Pat. Nos. 4,751,180 and 4,935,233, which are hereby incorporated by reference. A DNA sequence encoding a desired peptide linker may be inserted between, and in the same reading frame as, the DNA sequences of the invention, using any suitable conventional technique. For example, a chemically synthesized oligonucleotide encoding the linker may be ligated between the sequences. In particular embodiments, a fusion protein comprises from two to four soluble TSLP polypeptides, separated by peptide linkers.

Leucine-Zippers

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., *Science* 240:1759 (1988)), and have since been found in a variety of different proteins. Among the known leucine zippers are naturally occurring peptides and derivatives thereof that dimerize or trimerize.

The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science,* 243:1681 (1989)). Two nuclear transforming proteins, fos and jun, also exhibit zipper domains, as does the gene product of the murine proto-oncogene, c-myc (Landschulz et al., *Science,* 240:1759 (1988)). The products of the nuclear oncogenes fos and jun comprise zipper domains that preferentially form heterodimer (O'Shea et al., *Science,* 245:646 (1989)), (Turner and Tjian, *Science,* 243:1689 (1989)). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature,* 338:547 (1989); (Britton, *Nature,* 353:394 (1991)); (Delwart and Mosialos, *AIDS Research and Human Retroviruses,* 6:703 (1990)). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523 (1991)). Zipper domains have also been recently reported to play a role in oligomerization of heat-shock transcription factors (Rabindran et al., *Science* 259:230 (1993)).

Zipper domains fold as short, parallel coiled coils. (O'Shea et al., *Science* 254:539 (1991)). The general architecture of the parallel coiled coil has been well characterized, with a "knobs-into-holes" packing as proposed by (Crick, *Acta Crystallogr.,* 6:689)). The dimer formed by a zipper domain is stabilized by the heptad repeat, designated $(abcdefg)_n$ according to the notation of (McLachlan and Stewart, *J. Mol. Biol.,* 98:293 (1975)), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek et al., *Int. J. Peptide Res.,* 38:229 (1991)). (Lovejoy et al., *Science* 259:1288 (1993)) recently reported the synthesis of a triple-stranded α-helical bundle in which the helices run up-up-down. Their studies confirmed that hydrophobic stabilization energy provides the main driving force for the formation of coiled coils from helical monomers. These studies also indicate that electrostatic interactions contribute to the stoichiometry and geometry of coiled coils. Further discussion of the structure of leucine zippers is found in (Harbury et al., *Science,* 262:1401 (26 Nov. 1993)).

Examples of leucine zipper domains suitable for producing soluble oligomeric proteins are described in PCT application WO 94/10308, and the leucine zipper derived from lung surfactant protein D (SPD) described in (Hoppe et al., *FEBS Letters,* 344:191 (1994)), hereby incorporated by reference. The use of a modified leucine zipper that allows for stable trimerization of a heterologous protein fused thereto is described in (Fanslow et al., *Semin. Immunol.,* 6:267-278 (1994)). Recombinant fusion proteins comprising a soluble polypeptide fused to a leucine zipper peptide are expressed in suitable host cells, and the soluble oligomer that forms is recovered from the culture supernatant.

Certain leucine zipper moieties preferentially form trimers. One example is a leucine zipper derived from lung surfactant protein D (SPD), as described in (Hoppe et al., *FEBS Letters,* 344:191 (1994)) and in U.S. Pat. No. 5,716,805, hereby incorporated by reference in their entirety. This lung SPD-derived leucine zipper peptide comprises the amino acid sequence Pro Asp Val Ala Ser Leu Arg Gln Gln Val Glu Ala Leu Gln Gly Gln Val Gln His Leu Gln Ala Ala Phe Ser Gln Tyr (SEQ ID NO:4).

Another example of a leucine zipper that promotes trimerization is a peptide comprising the amino acid sequence Arg Met Lys Gln Ile Glu Asp Lys Ile Glu Glu Ile Leu Ser Lys Ile Tyr His Ile Glu Asn Glu Ile Ala Arg Ile Lys Lys Leu Ile Gly Glu Arg, (SEQ ID NO:5), as described in U.S. patent ide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained.

Other peptides derived from naturally occurring trimeric proteins may be employed in preparing trimeric oligomers. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Production of Polypeptides and Fragments Thereof

Expression, isolation and purification of the polypeptides and fragments of the invention may be accomplished by any suitable technique, including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site. Particular embodiments of mature proteins provided herein include, but are not limited to, proteins having the residue at position 16, 29, 35, 95, or 117 of SEQ ID NO:2 as the N-terminal amino acid.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in (Pouwels et al. *Cloning Vectors: A Laboratory Manual*, Elsevier, New York, (1985)). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615 (1978); and (Goeddel et al., *Nature* 281:544 (1979)), tryptophan (trp) promoter system (Goeddel et al., *Nucl. Acids Res.* 8:4057 (1980); and EP-A-36776) and tac promoter (Maniatis, *Molecular Cloning: A Laboratory Manual*, Cold Spring Harbor Laboratory, p. 412 (1982)). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Yeast Systems

Alternatively, the polypeptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073 (1980)) or other glycolytic enzymes (Hess et al., *J. Adv. Enzyme Reg.* 7:149 (1968)); and (Holland et al., *Biochem.* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in (Hitzeman, EPA-73,657). Another alternative is the glucose-repressible ADH2 promoter described by (Russell et al., *J. Biol. Chem.* 258:2674 (1982)) and (Beier et al., *Nature* 300:724 (1982)). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., (Kurjan et al., *Cell* 30:933 (1982)) and (Bitter et al., *Proc. Natl. Acad. Sci. USA* 81:5330 (1984)). Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by (Hinnen et al., *Proc. Natl. Acad. Sci. USA* 75:1929 (1978)). The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/nil uracil. Derepression of the ADH2 promoter occurs when glucose is exhausted from the medium.

Mammalian or Insect Systems

Mammalian or insect host cell culture systems also may be employed to express recombinant polypeptides. Bacculovirus systems for production of heterologous proteins in insect cells are reviewed by (Luckow and Summers, *Bio/Technology*, 6:47 (1988)). Established cell lines of mammalian origin also may be employed. Examples of suitable mammalian host cell lines include the COS-7 line of monkey kidney cells (ATCC CRL 1651) (Gluzman et al., *Cell* 23:175 (1981)), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by (McMahan et al., *EMBO J*, 10: 2821 (1991)).

Established methods for introducing DNA into mammalian cells have been described (Kaufman, R. J., *Large Scale Mammalian Cell Culture*, pp. 15-69 (1990)). Additional protocols using commercially available reagents, such as Lipofectamine lipid reagent (Gibco/BRL) or Lipofectamine-Plus lipid reagent, can be used to transfect cells (Feigner et al., *Proc. Natl. Acad. Sci. USA* 84:7413-7417 (1987)). In addition, electroporation can be used to transfect mammalian cells using conventional procedures, such as those in (Sambrook et al., *Molecular Cloning: A Laboratory Manual*, 2 ed. Vol. 1-3, Cold Spring Harbor Laboratory Press (1989)). Selection of stable transformants can be performed using methods known in the art, such as, for example, resistance to cytotoxic drugs. (Kaufman et al., *Meth. in Enzymology* 185:487-511 (1990)), describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220 (1980)). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113 (1978)); (Kaufman, *Meth. in Enzymology* (1990)). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, pp. 529-534 and PCT Application WO 97/25420 (1997)) and the tripartite leader (TPL) and VA gene RNAs from Adenovirus 2 (Gingeras et al., *J. Biol. Chem.* 257:13475-13491 (1982)). The internal ribosome entry site (IRES) sequences of viral origin allows dicistronic mRNAs to be translated efficiently (Oh and Samow, *Current Opinion in Genetics and Development* 3:295-300 (1993)); (Ramesh et al., *Nucleic Acids Research* 24:2697-2700 (1996)). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology* (1990)). Exemplary expression vectors that employ dicistronic mRNAs are pTR-DC/GFP described by (Mosser et al., *Biotechniques* 22:150-161 (1997)), and p2A5I described by (Morris et al., *Animal Cell Technology*, pp. 529-534 (1997)).

A useful high expression vector, pCAVNOT, has been described by (Mosley et al., *Cell* 59:335-348 (1989)). Other expression vectors for use in mammalian host cells can be constructed as disclosed by (Okayama and Berg, *Mol. Cell. Biol.* 3:280 (1983)). A useful system for stable high level expression of mammalian cDNAs in C127 murine mammary epithelial cells can be constructed substantially as described by (Cosman et al., *Mol. Immunol.* 23:935 (1986)). A useful high expression vector, PMLSV N1/N4, described by (Cosman et al., *Nature* 312:768 (1984)), has been deposited as ATCC 39890. Additional useful mammalian expression vectors are described in EP-A-0367566, and in WO 91/18982, incorporated by reference herein. In yet another alternative, the vectors can be derived from retroviruses.

Another useful expression vector, pFLAG$^7$, can be used. FLAG$^7$ technology is centered on the fusion of a low molecular weight (1 kD), hydrophilic, FLAG$^7$ marker peptide to the N-terminus of a recombinant protein expressed by pFLAG$^7$ expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in (Cosman et al., Nature 312:768 (1984)); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Purification

The invention also includes methods of isolating and purifying the polypeptides and fragments thereof.

Isolation and Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAF) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See (Berenson, et al. *J. Cell. Biochem.*, 10D:239 (1986)). Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Assays

The purified polypeptides of the invention (including proteins, polypeptides, fragments, variants, oligomers, and other forms) may be tested for the ability to bind TSLP receptors in any suitable assay, such as a conventional binding assay. To illustrate, the polypeptide may be labeled with a detectable reagent (e.g., a radionuclide, chromophore, enzyme that catalyzes a colorimetric or fluorometric reaction, and the like). The labeled polypeptide is contacted with cells expressing TSLP receptors. The cells then are washed to remove unbound labeled polypeptide, and the presence of cell-bound label is determined by a suitable technique, chosen according to the nature of the label.

One example of a binding assay procedure is as follows. A recombinant expression vector containing TSLP cDNA is constructed by methods known in the art. The mouse TSLP receptor comprises an N-terminal extracellular domain, a transmembrane region, and a C-terminal cytoplasmic domain. CV1-EBNA-1 cells in 10 cm$^2$ dishes are transfected with the recombinant expression vector. CV-1/EBNA-1 cells (ATCC CRL 10478) constitutively express EBV nuclear antigen-1 driven from the CMV immediate-early enhancer/promoter. CV1-EBNA-1 was derived from the African Green Monkey kidney cell line CV-1 (ATCC CCL 70), as described by (McMahan et al., *EMBO J.* 10:2821 (1991)).

The transfected cells are cultured for 24 hours, and the cells in each dish then are split into a 24-well plate. After culturing an additional 48 hours, the transfected cells (about 4×10$^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion protein made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc protein that has bound to the cells. In all assays, non-specific binding of $^{125}$I-antibody is assayed in the absence of the Fc fusion protein/Fc, as well as in the presence of the Fc fusion protein and a 200-fold molar excess of unlabeled mouse anti-human IgG antibody.

Cell-bound $^{125}$I-antibody is quantified on a Packard Autogamma counter. Affinity calculations (Scatchard, *Ann. N.Y. Acad. Sci.* 51:660 (1949)) are generated on RS/1 (BBN Software, Boston, Mass.) run on a Microvax computer.

Another type of suitable binding assay is a competitive binding assay. To illustrate, biological activity of a variant may be determined by assaying for the variant's ability to compete with the native protein for binding to TSLP receptors.

Competitive binding assays can be performed by conventional methodology. Reagents that may be employed in competitive binding assays include radiolabeled TSLP and intact cells expressing TSLP receptors (endogenous or recombinant) on the cell surface. For example, a radiolabeled soluble TSLP fragment can be used to compete with a soluble TSLP variant for binding to cell surface TSLP receptors. Instead of intact cells, one could substitute a soluble TSLP receptor/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J.

Another type of competitive binding assay utilizes radiolabeled soluble TSLP receptor, such as a soluble TSLP receptor/Fc fusion protein, and intact cells expressing endogenous or recombinant TSLP receptor. The radiolabeled TSLP receptor can be used to compete with the membrane bound TSLP receptor for soluble TSLP. Qualitative results can be obtained by competitive autoradiographic plate binding assays, while Scatchard plots (Scatchard, *Ann. N.Y. Acad. Sci.* 51:660 (1949)) may be utilized to generate quantitative results.

Use of Human TSLP Nucleic Acid or Oligonucleotides

In addition to being used to express polypeptides as described above, the nucleic acids of the invention, including DNA, RNA, mRNA and oligonucleotides thereof can be used:

as probes to identify nucleic acid encoding proteins having the ability to induce B lineage or T lineage cell proliferation;
to identify human chromosome number 5;
to map genes on human chromosome number 5;
to identify genes associated with certain diseases, syndromes, or other conditions associated with human chromosome number 5;
as single-stranded sense or antisense oligonucleotides, to inhibit expression of polypeptide encoded by the TSLP gene;
to help detect defective genes in an individual; and
for gene therapy.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO:1, from other mammalian species, are contemplated herein, probes based on the human DNA sequence of SEQ ID NO:1 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Chromosome Mapping

All or a portion of the nucleic acids of SEQ ID NO:1, including oligonucleotides, can be used by those skilled in the art using well-known techniques to identify the human chromosome 5, and the specific locus thereof, that may contain the DNA of other TSLP family members. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by using PCR and radiation hybridization. PCR is performed using the Whitehead Institute/MIT Center for Genome Research Genebridge4 panel of 93 radiation hybrids. Primers are used which lie within a putative exon, across an intron, or across an intron-exon fragment of the gene of interest and which amplify a product from human genomic DNA, but do not amplify, for example, control hamster genomic DNA. The results of the PCRs are converted into a data vector that is submitted to the Whitehead/MIT Radiation Mapping site on the internet. The data is scored and the chromosomal assignment and placement relative to known Sequence Tag Site (STS) markers on the radiation hybrid map is provided.

Identifying Associated Diseases

As set forth below, SEQ ID NO:1 has been mapped to the q21-q22 region of chromosome 5 by syntenic analysis of the murine gene. Thus, the nucleic acid of SEQ ID NO:1 or a fragment thereof can be used by one skilled in the art using well-known techniques to analyze abnormalities associated with human chromosome number 5 and, in particular, with the q21-q22 region of chromosome number 5, including Gardner syndrome, adenomatous polyposis coli, hereditary desmoid disease, Turcot syndrome, and colorectal cancer. This enables one to distinguish conditions in which this marker is rearranged or deleted. In addition, nucleotides of SEQ ID NO:1 or a fragment thereof can be used as a positional marker to map other genes of unknown location.

The DNA may be used in developing treatments for any disorder mediated (directly or indirectly) by defective or insufficient amounts of the genes corresponding to the nucleic acids of the invention. Disclosure herein of native nucleotide sequences permits the detection of defective genes, and the replacement thereof with normal genes. Defective genes may be detected in in vitro diagnostic assays, and by comparison of a native nucleotide sequence disclosed herein with that of a gene derived from a person suspected of harboring a defect in this gene.

Sense-Antisense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA (SEQ ID NO:1). Such a fragment generally comprises at least about 14 nucleotides, preferably from about 14 to about 30 nucleotides. The ability to derive an antisense or a sense oligonucleotide, based upon a cDNA sequence encoding a given protein is described in, for example, (Stein and Cohen, Cancer Res. 48:2659 (1988)) and (van der Krol et al., *Bio Techniques* 6:958 (1988)).

Binding of antisense or sense oligonucleotides to target nucleic acid sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, $CaPO_4$-mediated DNA transfection, electroporation, or by using gene transfer vectors such as Epstein-Barr virus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Use of Human TSLP Polypeptides and Fragmented Polypeptides

Uses include, but are not limited to, the following:
Purifying proteins and measuring activity thereof
Delivery Agents
Therapeutic and Research Reagents
Molecular weight and Isoelectric focusing markers
Controls for peptide fragmentation
Identification of unknown proteins
Preparation of Antibodies
Purification Reagents The polypeptide of the invention finds use as a protein purification reagent. For example, the polypeptides may be used to purify TSLP binding partners, such as human TSLP receptors. In particular embodiments, a polypeptide (in any form described herein that is capable of binding TSLP receptors) is attached to a solid support by conventional procedures. As one example, affinity chromatography columns containing functional groups that will react with functional groups on amino acid side chains of proteins are available (Pharmacia Biotech, Inc., Piscataway, N.J.). In an alternative, a TSLP polypeptide/Fc protein (as discussed above) is attached to Protein A- or Protein G-containing chromatography columns through interaction with the Fc moiety.

The polypeptide also finds use in purifying or identifying cells that express TSLP receptors on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing TSLP receptor expressing cells are contacted with the solid phase having the polypeptides thereon. Cells expressing TSLP receptor on the cell surface bind to the fixed polypeptides, and unbound cells then are washed away.

Alternatively, the polypeptides can be conjugated to a detectable moiety, then incubated with cells to be tested for TSLP receptor expression. After incubation, unbound labeled matter is removed and the presence or absence of the detectable moiety on the cells is determined.

In a further alternative, mixtures of cells suspected of containing TSLP receptors are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239 (1986)). Washing to remove unbound material, and the release of the bound cells, are performed using conventional methods.

Measuring Activity

Polypeptides also find use in measuring the biological activity of TSLP receptors in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a TSLP receptor that has been stored at different temperatures, or produced in different cell types. The proteins also may be used to determine whether biological activity is retained after modification of a TSLP receptor (e.g., chemical modification, truncation, mutation, etc.). The binding affinity of the modified TSLP receptor is compared to that of an unmodified TSLP receptor to detect any adverse impact of the modifications on biological activity of TSLP receptors. The biological activity of a TSLP receptor thus can be ascertained before it is used in a research study, for example.

Delivery Agents

The polypeptides also find use as carriers for delivering agents attached thereto to cells bearing TSLP receptors. Cells expressing TSLP receptors include those identified in thymus, spleen, kidney, and bone marrow. The polypeptides thus can be used to deliver diagnostic or therapeutic agents to such cells (or to other cell types found to express TSLP receptors on the cell surface) in in vitro or in vivo procedures.

Detectable (diagnostic) and therapeutic agents that may be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pb, $^{64}$Cu, and $^{67}$Cu.

Such agents may be attached to the polypeptide by any suitable conventional procedure. The polypeptide comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to polypeptides by using a suitable bifunctional chelating agent, for example.

Conjugates comprising polypeptides and a suitable diagnostic or therapeutic agent (preferably covalently linked) are thus prepared. The conjugates are administered or otherwise employed in an amount appropriate for the particular application.

Therapeutic Agents

Polypeptides of the invention may be used in developing treatments for any disorder mediated (directly or indirectly) by defective, or insufficient amounts of the polypeptides. These polypeptides may be administered to a mammal afflicted with such a disorder.

The polypeptides may also be employed in inhibiting the biological activity of TSLP receptors in in vitro or in vivo procedures. For example, a purified or modified polypeptide or a fragment thereof (e.g., modified TSLP polypeptides that bind the receptor but lack the ability to induce signaling) may be used to inhibit binding of endogenous TSLP to cell surface receptors. Biological effects that result from the binding of endogenous TSLP to receptors thus are inhibited.

In addition, TSLP receptor polypeptides may be administered to a mammal to treat a TSLP receptor-mediated disorder. Such TSLP receptor-mediated disorders include conditions caused (directly or indirectly) or exacerbated by TSLP receptors.

Compositions of the present invention may contain a polypeptide in any form described herein, such as native proteins, variants, derivatives, oligomers, and biologically active fragments. In particular embodiments, the composition comprises a soluble TSLP polypeptide or an oligomer comprising soluble TSLP polypeptides.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in (*Remington's Pharmaceutical Sciences*, 16th ed., Mack Publishing Company, Easton, Pa. (1980)).

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Compositions comprising nucleic acids in physiologically acceptable formulations are also contemplated. DNA may be formulated for injection, for example.

Research Agents

Another use of the polypeptide of the present invention is as a research tool for studying the biological effects that result from inhibiting TSLP/TSLP receptor interactions on different cell types. Polypeptides also may be employed in in vitro assays for detecting TSLP or TSLP receptors or the interactions thereof.

Another embodiment of the invention relates to uses of human TSLP to study B cell or T cell signal transduction. Human TSLP and other cytokines play a central role in B cell and T cell development and immune responses, including transducing cellular signals, stimulating cells to secrete cytokines, and inducing B cell and T cell proliferation. As such, alterations in the expression and/or activation of TSLP can have profound effects on a plethora of cellular processes, including, but not limited to, activation or inhibition of cell specific responses and proliferation. Expression of cloned TSLP or of catalytically inactive mutants of TSLP has been used to identify the role a particular protein plays in mediating specific signaling events.

Cellular signaling often involves a molecular activation cascade, during which a receptor propagates a ligand-receptor mediated signal by specifically activating intracellular kinases which phosphorylate target substrates. These substrates can themselves be kinases which become activated following phosphorylation. Alternatively, they can be adaptor molecules that facilitate down stream signaling through protein-protein interaction following phosphorylation. Regardless of the nature of the substrate molecule(s), expressed catalytically active versions of the TSLP ligand receptors can be used to identify what substrate(s) were recognized and activated by the TSLP ligand receptor(s). As such, these novel TSLP receptors can be used as reagents to identify novel molecules involved in signal transduction pathways.

In addition, TSLP can be used by one skilled in the art using well-known techniques to stimulate B lineage or T lineage cell proliferation (Ray et al., *Eur. J. Immunology* 26, 10-16 (1996)) and (Namikawa et al., *Blood* 87:1881-1890 (1996)), to expression clone the human TSLP receptor (Sims et al., *Science* 241:585-589 (1988)), to clone a related protein (Kozlosky et. al., *Cytokine* 9:540-549 (1997)) and (Lyman et al., *Blood* 10:2795-2801 (1994)), and to ex vivo expand cells (Piacibello et al., *Blood* 89:2644-2653 (1997)).

Uses Thereof

Thus, the present invention encompasses methods of stimulating B- and T-lymphocyte proliferation, where the method comprises incubating lymphocytes with human TSLP. In a further embodiment, the method comprises incubating lymphocytes with human TSLP and at least one other cytokine in vivo or in vitro. Preferably, the cytokine is selected from the group of IL-7, Steel Factor, Stem Cell Factor, Mast Cell Growth Factor or flt3-Ligand. More preferably the cytokine is IL-7.

The present invention also encompasses methods of stimulating lymphocyte development or lymphopoiesis, where the method comprises incubating progenitor cells, such as bone marrow-derived mononuclear cells, with human TSLP in vivo or in vitro. In a further embodiment, the method comprises incubating lymphocytes with human TSLP and at least one other cytokine. Preferably, the cytokine is selected from the group of IL-7, Steel Factor, Stem Cell Factor, Mast Cell Growth Factor or flt3-Ligand. More preferably the cytokine is IL-7.

Molecular Weight and Isoelectric Point Markers

The polypeptides of the present invention can be subjected to fragmentation into smaller peptides by chemical and enzymatic means, and the peptide fragments so produced can be used in the analysis of other proteins or polypeptides. For example, such peptide fragments can be used as peptide molecular weight markers, peptide isoelectric point markers, or in the analysis of the degree of peptide fragmentation. Thus, the invention also includes these polypeptides and peptide fragments, as well as kits to aid in the determination of the apparent molecular weight and isoelectric point of an unknown protein and kits to assess the degree of fragmentation of an unknown protein.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz.* 11:238-255 (1967)). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, *Achromobacter* protease I, Trypsin, *Staphylococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. *Achromobacter* protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44-50 (1981); T. Masaki et al., *Biochim. Biophys. Acta* 660:51-55 (1981)). Trypsin can cleave specifically on the carboxyl side of the arginine and lysine residues present within polypeptides of the invention. Enzymatic fragmentation may also occur with a protease that cleaves at multiple amino acid residues. For example, *Staphylococcus aureus* V8 protease can cleave specifically on the carboxyl side of the aspartic and glutamic acid residues present within polypeptides (D. W. Cleveland, *J. Biol. Chem.* 3:1102-1106 (1977)). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed. Glycosylation of polypeptides and peptide fragments of the invention in various cell types can result in variations of the molecular weight of these pieces, depending upon the extent of modification. The size of these pieces can be most heterogeneous with fragments of polypeptide derived from the extracellular portion of the polypeptide.

Consistent polypeptides and peptide fragments can be obtained by using polypeptides derived entirely from the transmembrane and cytoplasmic regions, pretreating with N-glycanase to remove glycosylation, or expressing the polypeptides in bacterial hosts.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

The polypeptides and the resultant fragmented peptides can be analyzed by methods including sedimentation, electrophoresis, chromatography, and mass spectrometry to determine their molecular weights. Because the unique amino acid sequence of each piece specifies a molecular weight, these pieces can thereafter serve as molecular weight markers using such analysis techniques to assist in the determination of the molecular weight of an unknown protein, polypeptides or fragments thereof. The molecular weight markers of the invention serve particularly well as molecular weight markers for the estimation of the apparent molecular weight of proteins that have similar apparent molecular weights and, consequently, allow increased accuracy in the determination of apparent molecular weight of proteins.

When the invention relates to the use of fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, *Nature* 227:680-685 (1970)). Conventionally, the method uses two separate lanes of a gel containing sodium dodecyl sulfate and a concentration of acrylamide between 6-20%. The ability to simultaneously resolve the marker and the sample under identical conditions allows for increased accuracy. It is understood, of course, that many different techniques can be used for the determination of the molecular weight of an unknown protein using polypeptides of the invention, and that this embodiment in no way limits the scope of the invention.

Each unglycosylated polypeptide or fragment thereof has a pI that is intrinsically determined by its unique amino acid sequence (which pI can be estimated by the skilled artisan using any of the computer programs designed to predict pI values currently available, calculated using any well-known amino acid pKa table, or measured empirically). Therefore these polypeptides and fragments thereof can serve as specific markers to assist in the determination of the isoelectric point of an unknown protein, polypeptide, or fragmented peptide using techniques such as isoelectric focusing. These polypeptide or fragmented peptide markers serve particularly well for the estimation of apparent isoelectric points of unknown proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the unknown protein under identical conditions allows for increased accuracy in the determination of the apparent isoelectric point of the unknown protein. This is of particular interest in techniques, such as two dimensional electrophoresis (T. D. Brock and M. T. Madigan, *Biology of Microorganisms* 76-77, Prentice Hall, 6d ed. (1991)), where the nature of the procedure dictates that any markers should be resolved simultaneously with the unknown protein. In addition, with such methods, these polypeptides and fragmented peptides thereof can assist in the determination of both the isoelectric point and molecular weight of an unknown protein or fragmented peptide.

Polypeptides and fragmented peptides can be visualized using two different methods that allow a discrimination between the unknown protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the unknown protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The unknown protein is also visualized by using a conventional staining procedure. The molar excess of unknown protein to polypeptide or fragmented peptide molecular weight markers of the invention is such that the conventional staining procedure predominantly detects the unknown protein. The level of these polypeptide or fragmented peptide molecular weight markers is such as to allow little or no detection of these markers by the conventional staining method. The preferred molar excess of unknown protein to polypeptide molecular weight markers of the invention is between 2 and 100,000 fold. More preferably, the preferred molar excess of unknown protein to these polypeptide molecular weight markers is between 10 and 10,000 fold and especially between 100 and 1,000 fold.

It is understood of course that many techniques can be used for the determination and detection of molecular weight and isoelectric point of an unknown protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., *J. Biol. Chem.* 252: 1102-1106 (1977)), such as by altering the time or temperature of the fragmentation reaction, can be used as a control for the extent of cleavage of an unknown protein. For example, cleavage of the same amount of polypeptide and unknown protein under identical conditions can allow for a direct comparison of the extent of fragmentation. Conditions that result in the complete fragmentation of the polypeptide can also result in complete fragmentation of the unknown protein.

As to the specific use of the polypeptides and fragmented peptides of the invention as molecular weight markers, the fragmentation of the polypeptide of SEQ ID NO:2 with cyanogen bromide generates a unique set of fragmented peptide molecular weight markers. The distribution of methionine residues determines the number of amino acids in each peptide and the unique amino acid composition of each peptide determines its molecular weight.

In addition, the preferred purified polypeptide of the invention (SEQ ID NO:2) has an observed molecular weight of approximately 21,000 Daltons.

Where an intact protein is used, the use of these polypeptide molecular weight markers allows increased accuracy in the determination of apparent molecular weight of proteins that have apparent molecular weights close to 21,000 Daltons. Where fragments are used, there is increased accuracy in determining molecular weight over the range of the molecular weights of the fragment.

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the unknown protein by chemical or enzymatic cleavage. Kits can further contain antibodies directed against polypeptides or fragments thereof of the invention.

Identification of Unknown Proteins

As set forth above, a polypeptide or peptide fingerprint can be entered into or compared to a database of known proteins to assist in the identification of the unknown protein using mass spectrometry (W. J. Hemel et al., *Proc. Natl. Acad. Sci. USA* 90:5011-5015 (1993); D. Fenyo et al., *Electrophoresis* 19:998-1005 (1998)). A variety of computer software programs to facilitate these comparisons are accessible via the Internet, such as Protein Prospector, MultiIdent, PeptideSearch, and ProFound. These programs allow the user to specify the cleavage agent and the molecular weights of the fragmented peptides within a designated tolerance. The programs compare these molecular weights to protein databases to assist in determining the identity of the unknown protein.

In addition, a polypeptide or peptide digest can be sequenced using tandem mass spectrometry (MS/MS) and the resulting sequence searched against databases (J. K. Eng, et al., *J. Am. Soc. Mass Spec.* 5:976-989 (1994); M. Mann and M. Wilm, *Anal. Chem.* 66:4390-4399 (1994); J. A. Taylor and R. S. Johnson, *Rapid Comm. Mass Spec.* 11:1067-1075 (1997)). Searching programs that can be used in this process exist on the Internet, such as Lutefisk 97, and the Protein Prospector, Peptide Search and ProFound programs described above. Therefore, adding the sequence of a gene and its predicted protein sequence and peptide fragments to a sequence database can aid in the identification of unknown proteins using tandem mass spectrometry.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9, Garland Publishing Inc., 2nd ed. (1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14, Garland Publishing Inc., 2nd ed. (1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, (Kennet et al., *Monoclonal Antibodies, Hybridomas: A New Dimension in Biological Analyses*, eds., Plenum Press, New York (1980); and Harlow and Land, *Antibodies: A Laboratory Manual*, eds., Cold Spring Harbor Laboratory Press, Cold Spring Harbor, N.Y., (1988)).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site)

derived from a human antibody. Procedures for the production of chimeric and further engineered monoclonal antibodies include those described in (Riechmann et al., Nature 332: 323 (1988), Liu et al., PNAS 84:3439 (1987), Larrick et al., Bio/Technology 7:934 (1989), and Winter and Harris, TIPS 14:139 (May 1993)). Procedures to generate antibodies transgenically can be found in GB 2,272,440, U.S. Pat. Nos. 5,569, 825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to TSLP receptors may be used to inhibit a biological activity that results from such binding. Such blocking antibodies may be identified using any suitable assay procedure, such as by testing antibodies for the ability to inhibit binding of TSLP to certain cells expressing the TSLP receptors. Examples of such cells are the B and T lymphoid cell lines 70Z/3 and 7B9, respectively. Alternatively, blocking antibodies may be identified in assays for the ability to inhibit a biological effect that results from binding of TSLP to TSLP receptors on target cells. Antibodies may be assayed for the ability to inhibit TSLP-mediated lysis of cells expressing TSLP receptors, for example.

Such an antibody may be employed in an in vitro procedure, or administered in vivo to inhibit a biological activity mediated by the entity that generated the antibody. Disorders caused or exacerbated (directly or indirectly) by the interaction of TSLP with cell surface TSLP receptors thus may be treated. A therapeutic method involves in vivo administration of a blocking antibody to a mammal in an amount effective in inhibiting TSLP-mediated biological activity. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, upon binding to cell surface TSLP receptors, induce biological effects (e.g., transduction of biological signals) similar to the biological effects induced when TSLP binds to cell surface TSLP receptors. Agonistic antibodies may be used to induce B lineage or T lineage cell proliferation.

Compositions comprising an antibody that is directed against human TSLP, and a physiologically acceptable diluent, excipient, or carrier, are provided herein. Suitable components of such compositions are as described above for compositions containing human TSLP proteins.

Also provided herein are conjugates comprising a detectable (e.g., diagnostic) or therapeutic agent, attached to the antibody. Examples of such agents are presented above. The conjugates find use in in vitro or in vivo procedures.

The following examples are provided to further illustrate particular embodiments of the invention, and are not to be construed as limiting the scope of the present invention.

Example 1

Isolation of the Nucleic Acid

Human TSLP nucleic acid sequence was obtained by sequencing EST IMAGE clone 1407260, accession #AA889581. This sequence suggested, in comparison to the murine TSLP sequence, that the EST clone was a partial clone. A number of cDNA libraries were screened with internal primers to determine a source of cDNA that could be used to obtain the missing 3' end of the TSLP cDNA clone. After 60 cycles of PCR using two internal primers of human TSLP sequence, the following cDNA libraries were positive for TSLP sequences: human testis, human foreskin fibroblasts, and fetal brain (weakly positive); while MoT, HS431, bone marrow, HPT4, HBT3, W126, Hut102, PBT, Sk Hep, human dermal fibroblast, Raji, human placenta, and KB libraries were all negative.

Using PCR on the human testis λgt10 library with an internal TSLP primer and a λgt10 vector primer, two clones (19E and 19F) with sequences identical to internal human TSLP sequences were isolated. Both clones had identical 5' ends but different length 3' ends. The coding as well as the non-coding sequences of clone 19E were identical to clone 19F; these clones differed in the length of the 3' non-coding region, where clone 19F was about 34 bp longer than 19E. Therefore, sequences from 19F were used to complete the 3' coding sequence of the human TSLP protein. This allowed for the identification of the C-terminal 15 amino acids not present in the EST. PCR was conducted according to conventional procedures.

Example 2

Purification of TSLP Polypeptide

TSLP-Specific ELISA

Serial dilutions of TSLP-containing samples (in 50 mM NaHCO$_3$, brought to pH 9 with NaOH) are coated onto Linbro/Titertek 96 well flat bottom E.I.A. microtitration plates (ICN Biomedicals Inc., Aurora, Ohio) at 100:1/well. After incubation at 4EC for 16 hours, the wells are washed six times with 200:1 PBS containing 0.05% Tween-20 (PBS-Tween). The wells are then incubated with FLAG'-TSLP receptor at 1 µg/ml in PBS-Tween with 5% fetal calf serum (FCS) for 90 minutes (100:1 per well), followed by washing as above. Next, each well is incubated with the anti-FLAG[7] (monoclonal antibody M2 at 1 µg/ml in PBS-Tween containing 5% FCS for 90 minutes (100:1 per well), followed by washing as above. Subsequently, wells are incubated with a polyclonal goat anti-mIgG1-specific horseradish peroxidase-conjugated antibody (a 1:5000 dilution of the commercial stock in PBS-Tween containing 5% FCS) for 90 minutes (100:1 per well). The HRP-conjugated antibody is obtained from Southern Biotechnology Associates, Inc., Birmingham, Ala. Wells then are washed six times, as above.

For development of the ELISA, a substrate mix [100:1 per well of a 1:1 premix of the TMB Peroxidase Substrate and Peroxidase Solution B (Kirkegaard Perry Laboratories, Gaithersburg, Md.)] is added to the wells. After sufficient color reaction, the enzymatic reaction is terminated by addition of 2 N H$_2$SO$_4$ (50:1 per well). Color intensity (indicating TSLP-TSLP receptor binding) is determined by measuring extinction at 450 nm on a V Max plate reader (Molecular Devices, Sunnyvale, Calif.).

Example 3

Amino Acid Sequence

The amino acid sequence of human TSLP was determined by translation of the complete human TSLP nucleotide sequence. The reading frame chosen was based on the homology of human TSLP with murine TSLP.

Example 4

DNA and Amino Acid Sequences

The human TSLP nucleic acid sequence was determined by standard double stranded sequencing of the composite sequence of EST IMAGE clone 1407260, accession #AA889581, and the additional 3' sequence from clone 19F.

The nucleotide sequence of the isolated human TSLP DNA and the amino acid sequence encoded thereby, are presented in SEQ ID NOs:1 and 2. The sequence of the entire human TSLP DNA fragment isolated by PCR corresponds to nucleotides 1 to 767 of SEQ ID NO:1, which encode amino acids 1 to 159 of SEQ ID NO:2.

The amino acid sequence in SEQ ID NO:2 bears significant similarity (49%) and identity (43%) to murine TSLP and weak homology to IL-7.

Example 5

Monoclonal Antibodies that Bind TSLP

This example illustrates a method for preparing monoclonal antibodies that bind TSLP. Suitable immunogens that may be employed in generating such antibodies include, but are not limited to, purified human TSLP polypeptide or an immunogenic fragment thereof such as the extracellular domain, or fusion proteins containing human TSLP (e.g., a soluble TSLP/Fc fusion protein).

Purified human TSLP can be used to generate monoclonal antibodies immunoreactive therewith, using conventional techniques such as those described in U.S. Pat. No. 4,411,993. Briefly, mice are immunized with human TSLP immunogen emulsified in complete Freund's adjuvant, and injected in amounts ranging from 10-100 µg subcutaneously or intraperitoneally. Ten to twelve days later, the immunized animals are boosted with additional human TSLP emulsified in incomplete Freund's adjuvant. Mice are periodically boosted thereafter on a weekly to bi-weekly immunization schedule. Serum samples are periodically taken by retro-orbital bleeding or tail-tip excision to test for TSLP antibodies by dot blot assay, ELISA (Enzyme-Linked Immunosorbent Assay) or inhibition of TSLP receptor binding.

Following detection of an appropriate antibody titer, positive animals are provided one last intravenous injection of human TSLP in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified TSLP by adaptations of the techniques disclosed in (Engvall et al., Immunochem. 8:871 (1971)) and in U.S. Pat. No. 4,703,004. A preferred screening technique is the antibody capture technique described in (Beckmann et al., J. Immunol. 144:4212 (1990)). Positive hybridoma cells can be injected intraperitoneally into syngeneic BALB/c mice to produce ascites containing high concentrations of anti-TSLP monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Protein A or Protein G can also be used, as can affinity chromatography based upon binding to TSLP.

Example 6

Northern Blot Analysis

The tissue distribution of human TSLP mRNA was investigated by Northern blot analysis, as follows. An aliquot of a radiolabeled probe was added to two different human multiple tissue Northern blots (Clontech, Palo Alto, Calif.; Biochain, Palo Alto, Calif.). The blots were hybridized in 10×Denhardts, 50 mM Tris pH 7.5, 900 mM NaCl, 0.1% Na pyrophosphate, 1% SDS, 200 µg/mL salmon sperm DNA. Hybridization was conducted overnight at 63EC in 50% formamide as previously described (March et al., Nature 315: 641-647 (1985)). The blots then were washed with 2×SSC, 0.1% SDS at 68EC for 30 minutes.

A single transcript of 1.4 kilobases (kb) was present in heart, lung, liver, skeletal muscle, kidney, pancreas, spleen, thymus, prostate, testes, ovary, small intestine, colon. Negative tissues were brain, placenta, and peripheral blood leukocytes. The cells and tissues with the highest levels of TSLP mRNA are heart, liver, prostate, and testes, as shown by comparison to control probing with a β-actin-specific probe.

Example 7

Binding Assay

Full length human TSLP can be expressed and tested for the ability to bind TSLP receptors. The binding assay can be conducted as follows.

A fusion protein comprising a leucine zipper peptide fused to the N-terminus of a soluble human TSLP polypeptide (LZ-TSLP) is employed in the assay. An expression construct is prepared, essentially as described for preparation of the FLAG[7] (TSLP) expression construct in (Wiley et al., Immunity, 3:673-682 (1995)); hereby incorporated by reference), except that DNA encoding the FLAG[7] peptide was replaced with a sequence encoding a modified leucine zipper that allows for trimerization. The construct, in expression vector pDC409, encodes a leader sequence derived from human cytomegalovirus, followed by the leucine zipper moiety fused to the N-terminus of a soluble human TSLP polypeptide. The LZ-TSLP is expressed in CHO cells, and purified from the culture supernatant.

The expression vector designated pDC409 is a mammalian expression vector derived from the pDC406 vector described in (McMahan et al., EMBO J. 10:2821-2832 (1991)) hereby incorporated by reference). Features added to pDC409 (compared to pDC406) include additional unique restriction sites in the multiple cloning site (mcs); three stop codons (one in each reading frame) positioned downstream of the mcs; and a T7 polymerase promoter, downstream of the mcs, that facilitates sequencing of DNA inserted into the mcs.

For expression of full length human TSLP protein, the entire coding region (i.e., the DNA sequence presented in SEQ ID NO:1) is amplified by polymerase chain reaction (PCR). The template employed in the PCR is the cDNA clone isolated from a human testis cDNA library, as described in Example 1. The isolated and amplified DNA is inserted into the expression vector pDC409, to yield a construct designated pDC409-TSLP.

LZ-TSLP polypeptide is employed to test the ability to bind to host cells expressing recombinant or endogenous TSLP receptors, as discussed above. Cells expressing TSLP receptor are cultured in DMEM supplemented with 10% fetal bovine serum, penicillin, streptomycin, and glutamine. Cells are incubated with LZ-TSLP (5 mg/ml) for about 1 hour. Following incubation, the cells are washed to remove unbound LZ-TSLP and incubated with a biotinylated anti-LZ monoclonal antibody (5 mg/ml), and phycoerythrin-conjugated streptavidin (1:400), before analysis by fluorescence-activated cell scanning (FACS). The cytometric analysis was conducted on a FACscan (Beckton Dickinson, San Jose, Calif.).

The cells expressing TSLP receptors showed significantly enhanced binding of LZ-TSLP, compared to the control cells not expressing TSLP receptors.

Example 8

Induction of T Cell Growth from Bone Marrow By TSLP and IL-7

Human TSLP, in combination with IL-7, induces the outgrowth of T cells from human bone marrow.

Human bone marrow-derived mononuclear cells (BM MNC) were isolated by centrifugation of whole bone marrow over Ficoll. BM MNC were cultured in McCoy's media supplemented with 10% fetal bovine serum, and amino acid and vitamin supplements, at a concentration ranging between $4.5-10 \times 10^5$ cells/ml in a total volume of 6 or 7 ml per flask (T25). Human TSLP (20 ng/ml) and other cytokines, i.e., IL-7, SLF (i.e., steel factor or stem cell factor, or mast cell growth factor), or flt3L, either alone or in combination, were added to the cultures at day 0. After 14 days and weekly thereafter, half the culture was removed for counting. Fresh media and cytokines were added to the cultures to return the total volume to 6 or 7 ml.

Harvested cells were also analyzed via flow cytometry fourteen days after culture and weekly thereafter, using antibodies specific for cell surface antigens. The antibodies used were specific for T cell antigens (i.e., the $\alpha\beta$T cell receptor, $\gamma\delta$T cell receptor, and CD3), B cell antigens (i.e., CD19 and surface IgM), Natural Killer cell antigens (i.e., CD56), monocyte antigens (i.e., CD14), and granulocyte antigens (i.e., CD15).

Addition of human TSLP and IL-7 to BM MNC cultures induced cellular growth as indicated in Table 1. At day 0, approximately 5% of BM MNC were T cells. After 2 weeks of culture with TSLP and IL-7, the cultures consisted of 70% CD3+ T cells. At day 21, 86% of the cells were CD3+ T cells. The cultures contained predominantly T cells until the termination of the experiment at day 42.

TABLE 1

| Treatment | Total Cell Yield (×10⁵) | | | | | |
|---|---|---|---|---|---|---|
| | Day 0 | Day 14 | Day 21 | Day 28 | Day 42 | Cumulative |
| | 13.5 | | | | | |
| Media | | 6 | 1.1 | 0.4 | 0.9 | 8.4 |
| TSLP | | 3.9 | 2.1 | 1 | 2.9 | 9.9 |
| IL-7 | | 4.2 | 7.4 | 4.4 | 4.6 | 20.6 |

TABLE 1-continued

| Treatment | Total Cell Yield (×10⁵) | | | | | |
|---|---|---|---|---|---|---|
| | Day 0 | Day 14 | Day 21 | Day 28 | Day 42 | Cumulative |
| IL-7 + TSLP | | 10.3 | 12.1 | 17.2 | 7.5 | 47.1 |
| SLF | | 3.7 | 4.3 | 1.1 | 0.9 | 10 |
| SLF + TSLP | | 5.4 | 6.9 | 1 | 1.6 | 14.9 |
| flt3L | | 6.3 | 2.3 | 2.8 | 1.8 | 13.2 |
| flt3L + TSLP | | 7.7 | 4.7 | 2.7 | 3.1 | 18.2 |

In another set of experiments, three separate batches of human TSLP tagged with His/FLAG[7] (TSLP 7489, TSLP 7811, or TSLP 7812) were tested alone or in combination with IL-7 for the ability to affect cell survival and expansion. BM MNC cultures were obtained from two separate, fresh bone marrow samples and seeded at a concentration of either $5 \times 10^5$ cells/ml (Group 1) or $10 \times 10^5$ cells/ml (Group 2). His/FLAW-tagged TSLP (20 mg/ml) and IL-7 were added to cultures as described above. TSLP combined with IL-7 resulted in expansion of BM MNC cultures as indicated in Table 2 (bone marrow sample 1) and Table 3 (bone marrow sample 2). By day 21, 80% of the expanded cell population consisted of CD4+ $\alpha\beta$+ or CD8+ $\alpha\beta$+ T cells. In four of the cultures treated with IL-7 and TSLP, cells expanded at such a rapid rate that an additional harvest was required at day 23 (Table 3). The cultures contained predominantly T cells until the termination of the experiments at 4-5 weeks.

TABLE 2

| Treatment | Total Cell Yield (×10⁵) | | | | | |
|---|---|---|---|---|---|---|
| | Day 0 | Day 14 | Day 21 | Day 28 | Day 35 | Cumulative |
| Group 1 (5 × 10⁵) | 17.5 | | | | | |
| Media | | 4 | 1.3 | 1.4 | ND* | 6.7 |
| IL-7 | | 8.4 | 6.5 | 7.1 | ND* | 22 |
| TSLP 7489 | | 4.4 | 1.5 | 1.2 | ND* | 7.1 |
| TSLP 7811 | | 5.2 | 1.7 | 1.2 | ND* | 8.1 |
| TSLP 7812 | | 2.8 | 1.4 | 2.3 | ND* | 6.5 |
| IL-7 + T7489 | | 12.4 | 9.1 | 8.3 | ND* | 29.8 |
| IL-7 + T7811 | | 10.5 | 5.3 | 8.4 | ND* | 24.2 |
| IL-7 + T7812 | | 9.7 | 6.5 | 4.7 | ND* | 20.9 |
| Group 2 (10 × 10⁵) | 35 | | | | | |
| Media | | 6.6 | 3.1 | 2.2 | ND* | 11.9 |
| IL-7 | | 14.8 | 10.1 | 3.7 | ND* | 32.3 |
| TSLP 7489 | | 11.5 | 3.3 | 2.9 | ND* | 17.7 |
| TSLP 7811 | | 13.3 | 2.8 | 3.1 | ND* | 19.2 |
| TSLP 7812 | | 13 | 3.2 | 2.6 | ND* | 18.8 |
| IL-7 + T7489 | | 25.6 | 17.7 | 8 | 10.9 | 62.2 |
| IL-7 + T7811 | | 18.8 | 16.8 | 10 | 15.7 | 61.3 |
| IL-7 + T7812 | | 22.4 | 13.5 | 10.4 | 11.6 | 57.9 |

*ND = not determined (culture exhausted)

TABLE 3

| Treatment | Total Cell Yield (×10⁵) | | | | | |
|---|---|---|---|---|---|---|
| | Day 0 | Day 14 | Day 21 | Day 23 | Day 28 | Day 35 | Cumulative |
| Group 1 (5 × 10⁵) | 17.5 | | | | | | |
| Media | | 3.1 | 0.9 | ND* | 0.8 | ND* | 4.8 |
| IL-7 | | 3.8 | 8.9 | ND* | 8 | ND* | 20.7 |
| TSLP 7489 | | 3 | 1.1 | ND* | 0.8 | ND* | 4.9 |
| TSLP 7811 | | 2.6 | 1.3 | ND* | ND* | ND* | 3.9 |
| TSLP 7812 | | 3.8 | 1.2 | ND* | 0.9 | ND* | 5.9 |

TABLE 3-continued

| Treatment | Day 0 | Day 14 | Day 21 | Day 23 | Day 28 | Day 35 | Cumulative |
|---|---|---|---|---|---|---|---|
| IL-7 + T7489 | | 8.9 | 80 | 39.4 | 18.2 | 21 | 167.5 |
| IL-7 + T7811 | | 6.2 | 12.5 | ND* | 16.7 | 14.3 | 49.7 |
| IL-7 + T7812 | | 7.1 | 14.5 | ND* | 11.1 | 11.6 | 44.3 |
| Group 2 (10 × 10⁵) | 35 | | | | | | |
| Media | | 6.6 | 1.9 | ND* | 1.8 | ND* | 10.3 |
| IL-7 | | 10.7 | 19 | ND* | 16.5 | 29.2 | 75.4 |
| TSLP 7489 | | 6.8 | 3.2 | ND* | 3.3 | ND* | 13.3 |
| TSLP 7811 | | 8.7 | 3.3 | ND* | 3.4 | ND* | 15.4 |
| TSLP 7812 | | 7.1 | 3.1 | ND* | 2.7 | ND* | 12.9 |
| IL-7 + T7489 | | 18.1 | 31.4 | 20 | 16.7 | 20.4 | 106.6 |
| IL-7 + T7811 | | 13.9 | 26.2 | 46.8 | 17.9 | 19.2 | 124 |
| IL-7 + T7812 | | 15.1 | 24.4 | 88.4 | 20.6 | 26.6 | 175.1 |

*ND = not determined (culture exhausted)

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention.

What is claimed is:

1. A method of stimulating lymphocyte proliferation, comprising incubating lymphocytes with IL-7 and a thymic stromal lymphopoietin (TSLP) polypeptide selected from the group consisting of:

(a) a polypeptide consisting of the amino acid sequence set forth in SEQ ID NO:2;
(b) a polypeptide consisting of the amino acid sequence of amino acids 29 through 159 or 35 through 159 of SEQ ID NO:2; and (c) a polypeptide encoded by the nucleic acid molecule consisting of the nucleotide sequence set forth in SEQ ID NO:1.

2. A method of stimulating lymphocyte development or lymphopoiesis comprising incubating progenitor cells with IL-7 and a thymic stromal lymphopoietin (TSLP) polypeptide selected from the group consisting of:
(a) a polypeptide consisting of the amino acid sequence set forth in SEQ ID NO:2;
(b) a polypeptide consisting of the amino acid sequence of amino acids 29 through 159 or 35 through 159 of SEQ ID NO:2; and
(c) a polypeptide encoded by the nucleic acid molecule consisting of the nucleotide sequence set forth in SEQ ID NO:1.

3. A method of inhibiting a thymic stromal lymphopoietin (TSLP)-mediated biological activity comprising contacting a TSLP polypeptide with an isolated antibody or antibody fragment that specifically binds to a TSLP polypeptide selected from the group consisting of:
(a) a polypeptide consisting of the amino acid sequence set forth in SEQ ID NO:2;
(b) a polypeptide consisting of the amino acid sequence of amino acids 29 through 159 or 35 through 159 of SEQ ID NO:2; and
(c) a polypeptide encoded by the nucleic acid molecule consisting of the nucleotide sequence set forth in SEQ ID NO:1, wherein said antibody or antibody fragment inhibits a TSLP-mediated biological activity selected from the group consisting of lymphopoiesis, lymphocyte development, or lymphocyte proliferation.

4. The method of claim 3, wherein said antibody or antibody fragment specifically binds to a polypeptide consisting of the amino acid sequence of amino acids 29 through 159 or 35 through 159 of SEQ ID NO:2.

5. The method of claim 3, wherein said antibody or antibody fragment specifically binds to a polypeptide encoded by the nucleic acid molecule consisting of the nucleotide sequence set forth in SEQ ID NO:1.

6. The method of claim 3, wherein the antibody is a monoclonal antibody.

7. The method of claim 3, wherein the antibody fragment is a Fab or F(ab')2.

8. The method of claim 3, wherein the method is carried out in vitro.

9. The method of claim 3, wherein the method is carried out in vivo.

10. The method of claim 3, wherein the antibody or antibody fragment is in a pharmaceutical composition further comprising a physiologically acceptable carrier.

11. The method of claim 3 wherein the inhibition of TSLP-mediated biological activity comprises blocking binding of TSLP to its receptor.

12. The method of claim 3 wherein TSLP-mediated biological activity is TSLP-mediated lymphocyte stimulation.

* * * * *

SEQUENCE LISTING

<160> NUMBER OF SEQ ID NOS: 5

<210> SEQ ID NO 1
<211> LENGTH: 743
<212> TYPE: DNA
<213> ORGANISM: Homo sapiens

<400> SEQUENCE: 1

```
gcagccagaa agctctggag catcagggag actccaactt aaggcaacag catgggtgaa      60
taagggcttc ctgtggactg gcaatgagag gcaaaacctg gtgcttgagc actggccccct    120 aaggcaggcc ttacagatct cttacactcg tggtgggaag agtttagtgt gaaactgggg    180
tggaattggg tgtccacgta tgttcccttt tgccttacta tatgttctgt cagtttcttt    240
caggaaaatc ttcatcttac aacttgtagg gctggtgtta acttacgact tcactaactg    300
tgactttgag aagattaaag cagcctatct cagtactatt tctaaagacc tgattacata    360
tatgagtggg accaaaagta ccgagttcaa caacaccgtc tcttgtagca atcggccaca    420
ttgccttact gaaatccaga gcctaacctt caatcccacc gccggctgcg cgtcgctcgc    480
caaagaaatg ttcgccatga aaactaaggc tgccttagct atctggtgcc caggctattc    540
ggaaactcag ataaatgcta ctcaggcaat gaagaagagg agaaaaagga aagtcacaac    600
caataaatgt ctggaacaag tgtcacaatt acaaggattg tggcgtcgct tcaatcgacc    660
tttactgaaa aacagtaaa ccatctttat tatggtcata tttcacagcc caaataaat    720 catctttatt aagtaaaaaa aaa                                            743
```

<210> SEQ ID NO 2
<211> LENGTH: 159
<212> TYPE: PRT
<213> ORGANISM: Homo sapiens

<400> SEQUENCE: 2

```
Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30
```

```
Asn Cys Asp Phe Glu Lys Ile Lys Ala Ala Tyr Leu Ser Thr Ile Ser
            35                  40                  45

Lys Asp Leu Ile Thr Tyr Met Ser Gly Thr Lys Ser Thr Glu Phe Asn
 50                  55                  60

Asn Thr Val Ser Cys Ser Asn Arg Pro His Cys Leu Thr Glu Ile Gln
 65                  70                  75                  80

Ser Leu Thr Phe Asn Pro Thr Ala Gly Cys Ala Ser Leu Ala Lys Glu
                 85                  90                  95

Met Phe Ala Met Lys Thr Lys Ala Leu Ala Ile Trp Cys Pro Gly
                100                 105                 110

Tyr Ser Glu Thr Gln Ile Asn Ala Thr Gln Ala Met Lys Lys Arg Arg
            115                 120                 125

Lys Arg Lys Val Thr Thr Asn Lys Cys Leu Glu Gln Val Ser Gln Leu
        130                 135                 140

Gln Gly Leu Trp Arg Arg Phe Asn Arg Pro Leu Leu Lys Gln Gln
145                 150                 155

<210> SEQ ID NO 3
<211> LENGTH: 8
<212> TYPE: PRT
<213> ORGANISM: Artificial sequence
<220> FEATURE:
<223> OTHER INFORMATION: antigenic peptide used in fusion proteins

<400> SEQUENCE: 3

Asp Tyr Lys Asp Asp Asp Asp Lys
1               5

<210> SEQ ID NO 4
<211> LENGTH: 27
<212> TYPE: PRT
<213> ORGANISM: Artificial sequence
<220> FEATURE:
<223> OTHER INFORMATION: leucine zipper polypeptide

<400> SEQUENCE: 4

Pro Asp Val Ala Ser Leu Arg Gln Gln Val Glu Ala Leu Gln Gly Gln
1               5                   10                  15

Val Gln His Leu Gln Ala Ala Phe Ser Gln Tyr
            20                  25

<210> SEQ ID NO 5
<211> LENGTH: 33
<212> TYPE: PRT
<213> ORGANISM: Artificial sequence
<220> FEATURE:
<223> OTHER INFORMATION: leucine zipper polypeptide

<400> SEQUENCE: 5

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg
```